US005977103A

United States Patent [19]

Adams et al.

[11] Patent Number: 5,977,103

[45] Date of Patent: Nov. 2, 1999

[54] SUBSTITUTED IMIDAZOLE COMPOUNDS

[75] Inventors: Jerry L. Adams, Wayne; Jeffrey C. Boehm, King of Prussia; Dennis Lee, Swarthmore, all of Pa.

[73] Assignee: SmithKline Beecham Corporation, Philadelphia, Pa.

[21] Appl. No.: 09/101,531

[22] PCT Filed: Jan. 10, 1997

[86] PCT No.: PCT/US97/00500

§ 371 Date: Nov. 13, 1998

§ 102(e) Date: Nov. 13, 1998

[87] PCT Pub. No.: WO97/25045

PCT Pub. Date: Jul. 17, 1997

Related U.S. Application Data

[60] Provisional application No. 60/014,952, Apr. 5, 1996, and provisional application No. 60/009,907, Jan. 11, 1996.

[51] Int. Cl.[6] ........................ A61K 31/47; C07D 401/02; C07D 413/14

[52] U.S. Cl. ....................... 514/235.2; 514/307; 514/314; 546/141; 546/148; 546/153; 546/167; 544/128

[58] Field of Search ............................ 544/128; 546/148, 546/167; 514/235.2

[56] References Cited

U.S. PATENT DOCUMENTS

| | | |
|---|---|---|
| 2,748,119 | 4/1956 | Rorig . |
| 3,557,114 | 1/1971 | Bicking . |
| 3,707,475 | 12/1972 | Lombardino . |
| 3,772,441 | 11/1973 | Lombardino . |
| 3,929,807 | 12/1975 | Fitzi . |
| 3,940,486 | 2/1976 | Fitzi . |
| 4,058,614 | 11/1977 | Baldwin . |
| 4,199,592 | 4/1980 | Cherkofsky . |
| 4,447,431 | 5/1984 | Sallman . |
| 4,503,065 | 3/1985 | Wilkerson . |
| 4,565,875 | 1/1986 | Cavender . |
| 4,686,231 | 8/1987 | Bender et al. . |
| 4,822,805 | 4/1989 | Tasasugi et al. . |
| 5,593,991 | 1/1997 | Adams et al. . |
| 5,593,992 | 1/1997 | Adams et al. . |
| 5,656,644 | 8/1997 | Adams et al. . |
| 5,658,903 | 8/1997 | Adams et al. . |
| 5,663,334 | 9/1997 | Adams et al. . |
| 5,670,527 | 9/1997 | Adams et al. . |
| 5,686,455 | 11/1997 | Adams et al. . |
| 5,716,955 | 2/1998 | Adams et al. . |
| 5,739,143 | 4/1998 | Adams et al. . |
| 5,756,499 | 5/1998 | Adams et al. . |

FOREIGN PATENT DOCUMENTS

| | | |
|---|---|---|
| WO92/10190 | 7/1992 | WIPO . |
| WO92/10498 | 8/1992 | WIPO . |
| WO 95/09852 | 3/1995 | WIPO . |
| WO 95/09847 | 4/1995 | WIPO . |
| WO95/02591 | 4/1995 | WIPO . |
| Wo 95/09853 | 4/1995 | WIPO . |
| WO95/02591 | 5/1995 | WIPO . |
| WO 95/09851 | 6/1995 | WIPO . |
| WO96/21452 | 3/1996 | WIPO . |
| WO96/21654 | 5/1996 | WIPO . |
| WO96/40143 | 6/1996 | WIPO . |
| WO64/25046 | 10/1997 | WIPO . |
| WO97/25045 | 10/1997 | WIPO . |
| WO97/25047 | 10/1997 | WIPO . |
| WO97/25048 | 10/1997 | WIPO . |
| WO97/35856 | 11/1997 | WIPO . |
| WO97/35855 | 12/1997 | WIPO . |
| WO98/22109 | 3/1998 | WIPO . |

OTHER PUBLICATIONS

Dinarello et al., Rev.Infect.Disease, 6, p.51 (1984).
Dinarello, J.Clin.Immun., 5(5), p. 287–297 (1985).
R.P.Soni, Aust.J.Chem., 35, p. 1493–6 (1982).
Poli et al., Proc.Nat'l Acad.Sci., 87, p. 782–784 (1990).
VanLeusen et al., J.O.C., 42, p. 1153 (1977).
Kumada et al., Tetrahedron Letters, 22, p.5319 (1981).
Pridgen, J.Org.Chem., 47, p.4319 (1982).
Stille,J.Amer.Chem.Soc., 109, p.5478 (1978).
Fischer et al., Rec.Trav.Chim.Pays.Bas., 84, p.439 (1965).
Snieckus, V., Tetrahedron Letters, 29, 2135 (1988).
Terashimia, M., Chem.Pharm.Bull., 11, p.4755 (1985).
Thompson, W.J., et al., J.Org.Chem., 49, p. 5237 (1984).
Garigipati, R., Tetrahedron Letters, 31,p.190 (1989).
Engel & Steglich, Liebigs Ann. Chem., 1916 (1978).
Strzybny et al., J. Org. Chem., 28, p.3381 (1963).
Zavyalov, et al., Khim Farm Zh, 26(3), p. 88 (1992) (With Translation).
Colotta et al., J. Immunol., 132(2), p.936 (1984).
Simon et al., J. Immunol. Methods, 84, p. 85 (1985).
Becker et al., J. Immunol., 147, p. 4307 (1991).
Gilbert, Synthesis, pp. 30–32 (1972).
Morton et al., Tetrahedron Letters, 4123 (1982).
Armarego, W. J. Chem. Soc., (JCSOA9) p. 561 (1962).
Kawasaki et al., J. Bio. Chem., 272(30), pp. 18518–18521 (1994).
Uno, Bull. Chem. Soc. Japan., vol. 69, pp. 1763–1767 (1996).
Katrutzky, Synthesis, pp. 45–47 (1993).
Johnson, P.A., J.Chem.Soc., Perkin Trans., vol. 1, pp.895–905 (1996).
Ishibashi, Chem. Pharm. Bull., 37(8), pp. 2214–2216 (1989).

*Primary Examiner*—Robert W. Ramsuer
*Attorney, Agent, or Firm*—Dara L. Dinner; Stephen Venetianer; Charles M. Kinzig

[57] ABSTRACT

This invention relates to a novel group of imidazole compounds, processes for the preparation thereof, the use thereof in treating cytokine mediated diseases and pharmaceutical compositions for use in such therapy.

30 Claims, No Drawings

SUBSTITUTED IMIDAZOLE COMPOUNDS

RELATED APPLICATIONS

This application is the §371 national stage entry of PCT/US97/00500, filed Jan. 10, 1997, which claims the benefit of provisional applications U.S. Ser. No. 60/014,952 filed, Apr. 5, 1996 and U.S. Ser. No. 60/009,907, filed Jan. 11, 1996.

This invention relates to a novel group of imidazole compounds, processes for the preparation thereof, the use thereof in treating cytokine mediated diseases and pharmaceutical compositions for use in such therapy.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease,* 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology,* 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. Monokines, such as TNF, have been shown to activate HIV replication in monocytes and/or macrophages [See Poli, et al., Proc. Natl. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11 b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppressive anti-inflammatory drugs, i.e. compounds which are capable of inhibiting cytokines, such as IL-1, IL-6, IL-8 and TNF.

SUMMARY OF THE INVENTION

This invention relates to the novel compounds of Formula (I) and pharmaceutical compositions comprising a compound of Formula (I) and a pharmaceutically acceptable diluent or carrier.

This invention relates to a method of treating a CSBP/RK/p38 kinase mediated disease, in a mammal in need thereof, which comprises administering to said mammal an effective amount of a compound of Formula (I).

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides a compound of Formula (I):

(I)

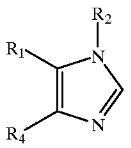

$R_1$ is 4-pyridyl, pyrimidinyl, quinolyl, isoquinolinyl, quinazolin4-yl, 1-imidazolyl or 1-benzimidazolyl ring, which ring is substituted with —Y—$R_a$ and optionally with an additional independent substituent selected from $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_b$, or $NHR_a$;

Y is oxygen or sulfur;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —$C(Z)NR_7R_{17}$, —$C(Z)OR_{16}$, —$(CR_{10}R_{20})_vCOR_{12}$, —$SR_5$, —$SOR_5$, —$OR_{12}$, halo-substituted-$C_{1-4}$ alkyl, $C_{1-4}$ alkyl, —$ZC(Z)R_{12}$, —$NR_{10}C(Z)R_{16}$, or —$(CR_{10}R_{20})_vNR_{10}R_{20}$ and which, for other positions of substitution, is halogen, cyano, —$C(Z)NR_{13}R_{14}$, —$C(Z)OR_3$, —$(CR_{10}R_{20})_{m''}COR_3$, —$S(O)_mR_3$, —$OR_3$, halo-substituted-$C_{1-4}$alkyl, —$C_{1-4}$alkyl, —$(CR_{10}R_{20})_{m''}NR_{10}C(Z)R_3$, —$NR_{10}S(O)_{m'}R_8$, —$NR_{10}S(O)_{m'}NR_7R_{17}$, —$ZC(Z)R_3$ or —$(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_2$ is —$(CR_{10}R_{20})_{n'}OR_9$, heterocyclyl, heterocyclyl$C_{1-10}$ alkyl, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$ cycloalkenyl-$C_{1-10}$-alkyl, aryl, aryl$C_{1-10}$ alkyl, heteroaryl, heteroaryl-$C_{1-10}$-alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the aryl, arylalkyl, heteroaryl, heteroaryl alkyl, cyclcoalkyl, cycloalkyl alkyl, heterocyclic and heterocyclic alkyl groups may be optionally substituted;

n is an integer having a value of 1 to 10;

n' is 0, or an integer having a value of 1 to 10;

Z is oxygen or sulfur;

$R_a$ is aryl, aryl$C_{1-6}$alkyl, heterocyclic, heterocyclyl$C_{1-6}$ alkyl, heteroaryl, heteroaryl$C_{1-6}$alkyl, wherein each of these moities may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$SOR_5$ being —SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$_{1-4}$alkyl, heterocyclyl, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

$R_9$ is hydrogen, —$C(Z)R_{11}$ or optionally substituted $C_{1-10}$ alkyl, $S(O)_2R_{18}$, optionally substituted aryl or optionally substituted aryl-$C_{1-4}$ allyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or C(Z)—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl, $_{1-10}$ alkyl, heterocyclyl, heterocyclyl-$C_{1-10}$alkyl, heteroaryl or heteroaryl$_{1-10}$alkyl;

$R_{19}$ is hydrogen, cyano, $C_{1-4}$ alkyl, $C_{3-7}$ cycloalkyl or aryl;

or a pharmaceutically acceptable salt thereof.

DETAILED DESCRIPTION OF THE INVENTION

In Formula (I), suitable $R_1$ moieties includes 4-pyridyl, 4-pyrimidinyl, 4-quinolyl, 6-isoquinolinyl, 4-quinazolinyl, 1-imidazolyl and 1-benzimidazolyl rings, of which the 4-pyridyl, 4-pyrimidinyl and 4-quinolyl rings are preferred. More preferred is the 4-pyrimidinyl or 4-pyridyl moiety, and most preferred is the 4-pyrimidinyl ring.

The $R_1$ moiety is substituted with the —Y—$R_a$ group wherein Y is oxygen or sulfur, and $R_a$ is aryl, aryl$C_{1-6}$alkyl, heterocyclic, heterocyclic$C_{1-6}$ alkyl, heteroaryl, or heteroaryl$C_{1-6}$alkyl; and wherein each of the $R_a$ moieties may be optionally substituted as defined below.

When $R_a$ is aryl, it is preferably phenyl or napthyl. When $R_a$ is arylalkyl, it it is preferably benzyl or napthylmethyl. When $R_a$ is a heterocyclic or heterocyclic alkyl moiety, the heterocyclic portion is preferably pyrrolindinyl, piperidine, morpholino, tetrahydropyran, tetrahydrothiopyranyl, tetrahydrothipyransulfinyl, tetrahydrothio-pyransulfonyl, pyrrolindinyl, indole, or piperonyl ring. It is noted that the heterocyclic rings herein may contain unsaturation, such as in a tryptamine ring.

When $R_a$ is a heteroaryl ring as defined below, it is preferably a pyridine or tetrazole ring.

The $R_a$ aryl, heterocyclic and heteroaryl rings may be optionally substituted one or more times, preferably one to three times. independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $C_{1-4}$ alkoxy, such as methoxy or ethoxy; $S(O)_m$alkyl and $S(O)_m$aryl (wherein m is 0, 1, or 2); $C(O)OR_{11}$, such as $C(O)C_{1-4}$ alkyl or C(O)OH moieties; $C(O)R_{11}$; —$OC(O)R_c$; —O—$(CH_2)$s—O—, such as in a ketal or dioxyalkylene bridge; amino; mono- and di-$C_{1-6}$ alkylsubstituted amino; —$N(R_{10})C(O)R_b$; —$C(O)NR_{10}R_{20}$; cyano, nitro, or an N-heterocyclyl ring which ring has from 5 to 7 members and optionally contains an additional heteroatom selected from oxygen, sulfur or $NR_{15}$; aryl, such as phenyl; an optionally substituted arylalkyl, such as benzyl or phenethyl; aryloxy, such as phenoxy; or arylalkyloxy such as benzyloxy.

$R_b$ is suitably hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety; all of which may be optionally substituted as defined below.

$R_c$ is suitably an $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted as defined below.

Suitable $R_a$ groups include,but are not limited to, benzyl, halosubstituted benzyl, napthylmethyl, phenyl, halosubstituted phenyl, aminocarbonylphenyl, alkylphenyl, cyanophenyl, alkylthiophenyl, hydroxyphenyl, alkoxyphenyl, phenoxyphenyl, benzyloxyphenyl, phenylphenyl, methylenedioxyphenyl, trifluoromethylphenyl, methylsulfonylphenyl, tetrazole, methyltetrazolyl, morpholinopropyl, piperonyl, piperidin-4-yl, alkyl substituted piperidine, such as 1-methyl piperidine, or 2,2,6,6-tetramethylpiperidin-4-yl.

It is recognized that the $R_1$ group may additionally be substituted one or more times independently by $C_{1-4}$ alkyl, halo, OH, $C_{1-4}$ alkoxy, $C_{1-4}$ alkylthio, $C_{1-4}$ alkylsulfinyl, $CH_2OR_{12}$, amino, mono- and di-$C_{1-6}$ alkylsubstituted amino, $N(R_{10})C(O)R_b$, $NHR_a$ or an N-heterocyclyl ring which ring has from 5 to 7 members and optionally contains an additional heteroatom selected from oxygen, sulfur or $NR_{15}$.

When the additional $R_1$ optional substituent is $N(R_{10})C(O)$ $R_b$, $R_b$ is preferably $C_{1-6}$ alkyl; preferably $R_{10}$ is hydrogen. It is also recognized that the $R_b$ moieties, in particular the $C_{1-6}$ alkyl group may be optionally substituted, preferably from one to three times, preferably with halogen, such as fluorine, as in trifluoromethyl or trifluroethyl.

The preferred ring placement on the $R_1$ substituent for $YR_a$, on the 4-pyridyl derivative is the 2-position, and a preferred ring placement on the 4-pyrimidinyl ring is also at the 2-position.

Suitably, $R_4$ is phenyl, naphth-1-yl or naphth-2-yl, or a heteroaryl, which is optionally substituted by one or two substituents. More preferably $R_4$ is a phenyl or naphthyl ring. Suitable substitutions for $R_4$ when this is a 4-phenyl, 4-naphth-1-yl, 5-naphth-2-yl or 6-naphth-2-yl moiety are one or two substituents each of which are independently selected from halogen, —$SR_5$, —$SOR_5$, —$OR_{12}$, $CF_3$, or —$(CR_{10}R_{20})_vNR_{10}R_{20}$, and for other positions of substitution on these rings preferred substitution is halogen, —$S(O)_mR_3$, —$OR_3$, $CF_3$, —$(CR_{10}R_{20})_{m''}NR_{13}R_{14}$, —$NR_{10}C(Z)R_3$ and —$NR_{10}S(O)_{m'}R_8$. Preferred substituents for the 4-position in phenyl and naphth-1-yl and on the 5-position in naphth-2-yl include halogen, especially fluoro and chloro and —$SR_5$ and —$SOR_5$ wherein $R_5$ is preferably a $C_{1-2}$ alkyl, more preferably methyl; of which the fluoro and chloro is more preferred, and most especially preferred is fluoro. Preferred substituents for the 3-position in phenyl and naphth-1-yl rings include: halogen, especially fluoro and chloro; —$OR_3$, especially $C_{1-4}$ alkoxy; $CF_3$, $NR_{10}R_{20}$, such as amino; $NR_{10}C(Z)R_3$, especially —$NHCO(C_{1-10}$ alkyl); —$NR_{10}S(O)_{m'}R_8$, especially $NHSO_2(C_{1-10}$ alkyl), and —$SR_3$ and —$SOR_3$ wherein $R_3$ is preferably a $C_{1-2}$ alkyl, more preferably methyl. When the phenyl ring is disubstituted preferably it is two independent halogen moieties, such as fluoro and chloro, preferably di-chloro and more preferably in the 3,4-position. It is also preferred that for the 3-position of both the —$OR_3$ and —$ZC(Z)R_3$ moietites, $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is a 4-fluorophenyl.

In Formula (I), Z is oxygen or sulfur, preferably oxygen.

Suitably, $R_2$ is —$(CR_{10}R_{20})_{n'}$ $OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}OC(Z)R_{11}$, $(CR_{10}R_{20})$ $_n NR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkylalkyl, aryl, arylalkyl, heteroaryl, heteroarylalkyl, heterocyclic, and heterocyclic alkyl moieties may be optionally substituted.

Suitably n is an integer having a value of 1 to 10, m is 0, or the integer 1 or 2; n' is 0, or an integer having a value of 1 to 10; and m' is 1 or 2. Preferably n is 1 to 4.

Preferably $R_2$ is an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{20})_nC(Z)OR_{11}$ group, $(CR_{10}R_{20})_nNR_{13}R_{14}$, $(CR_{10}R_{20})_nNHS(O)_2R_{18}$, $(CR_{10}R_{20})_nS(O)_mR_{18}$, an optionally substituted aryl; an optionally substituted aryl$C_{1-10}$ alkyl, $(CR_{10}R_{20})_nOR_{11}$, $(CR_{10}R_{20})_nC(Z)R_{11}$, or $(CR_{10}R_{20})_nC(=NOR_6)R_{11}$ group.

More preferably $R_2$ is an optionally substituted heterocyclyl ring, and optionally substituted heterocyclyl$C_{1-10}$ alkyl, optionally substituted aryl, an optionally substituted $C_{3-7}$cycloalkyl, an optionally substituted $C_{3-7}$cycloalkyl $C_{1-10}$ alkyl, $(CR_{10}R_{20})_nNR_{13}R_{14}$, or $(CR_{10}R_{20})_nC(Z)OR_{11}$ group.

When $R_2$ is an optionally substituted heterocyclyl the ring is preferably a morpholino, pyrrolidinyl, or a piperidinyl group. When the ring is optionally substituted the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl—wherein the aryl or aryl alkyl moieties themselves miay be optionally substituted (as in the definition section below); $C(O)OR_{11}$, such as the $C(O)C_{1-4}$ alkyl or C(O)OH moieties: C(O)H, $C(O)C_{1-4}$ alkyl, hydroxy substituted $C_{1-10}$ alkyl, $C_{1-10}$ alkoxy, $S(O)_mC_{1-4}$ alkyl (wherein m is 0, 1, or 2), $NR_{10}R_{20}$ (wherein $R_{10}$ and $R_{20}$ are independently hydrogen or $C_{1-4}$alkyl).

Preferably if the ring is a piperidine, the ring is attached to the imidazole at the 4-position, and the substituents are directly on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine. Similarly, if the ring is a pyrrole, the ring is attached to the imidazole at the 3-position, and the substituents are all directly on the available nitrogen.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties. The heterocyclic ring herein is also optionally substituted in a similar manner to that indicated above for the direct attachment of the heterocyclyl.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_4$ or $C_6$ ring, most preferably a $C_6$ ring, which ring is optionally substituted. The cycloalkyl ring may be optionally substituted one to three times independently by halogen, such as fluorine, chlorine, bromine or iodine; hydroxy; $C_{1-10}$ alkoxy, such as methoxy or ethoxy; $S(O)_m$ alkyl, wherein m is 0, 1, or 2, such as methyl thio, methylsulfinyl or methyl sulfonyl; $S(O)_m$ aryl; cyano, nitro, amino, mono & di-substituted amino, such as in the $NR_7R_{17}$ group, wherein $R_7$ and $R_{17}$ are as defined in Formula (I), or where the $R_7R_{17}$ may cyclize together with the nitrogen to which they are attached to form a 5 to 7 membered ring which optionally includes an additional heteroatom selected from oxygen, sulfur or $NR_{15}$ (and $R_{15}$ is as defined for Formula (I)); $N(R_{10})C(O)X_1$(wherein $R_{10}$ is as defined for Formula (I)), and $X_1$ is $C_{1-4}$ alkyl, aryl or aryl$C_{1-4}$ alkyl); $N(R_{10})C(O)$ aryl; $C_{1-10}$ alkyl, such as methyl, ethyl, propyl, isopropyl, or t-butyl; optionally substituted alkyl wherein the substituents are halogen, (such as $CF_3$), hydroxy, nitro, cyano, amino, mono & di-substituted amino, such as in the $NR_7R_{17}$ group, S(O)m alkyl and S(O)m aryl, wherein m is 0, 1 or 2; optionally substituted alkylene, such as ethylene or propylene; optinally substituted alkyne, such as ethyne; $C(O)OR_{11}$ (wherein $R_{11}$ is as defined in Formula (I)), such as the free acid or methyl ester derivative; the group $R_e$; —C(O)H; =O; =N—$OR_{11}$; —N(H)—OH (or substituted alkyl or aryl derivatives thereof on the nitrogen or the oxime moiety); —N($OR_d$)—C(O)—$R_f$, an optionally substituted aryl, such as phenyl; an optionally substituted aryl$C_{1-4}$alkyl, such as benzyl of phenethyl; an optionally substituted heterocycle or heterocyclic $C_{1-4}$alkyl, and further these aryl, arylalkyl, heterocyclic, and heterocyclic alkyl moieties are optionally substituted one to two times by halogen, hydroxy, $C_{1-10}$ alkoxy, $S(O)_m$ alkyl, cyano, nitro, amino, mono & di-substituted amino, such as in the $NR_7R_{17}$ group, an alkyl, halosubstituted alkyl.

Suitably $R_d$ is hydrogen, a pharmaceutically acceptable cation, aroyl or a $C_{1-10}$ alkanoyl group.

Suitably $R_e$ is a 1,3-dioxyalkylene group of the formula —O—$(CH_2)_s$—O—, wherein s is 1 to 3, preferably s is 2 yielding a 1,3-dioxyethylene moiety, or ketal functionality.

Suitably $R_f$ is $NR_{21}R_{22}$; alkyl $_{1-6}$; halosubstituted alkyl 1-6; hydroxy substituted alkyl $_{1-6}$; alkenyl $_{2-6}$; aryl or heteroaryl optionally substituted by halogen, alkyl $_{1-6}$, halosubstituted alkyl $_{1-6}$, hydroxyl, or alkoxy $_{1-6}$.

Suitably $R_{21}$ is hydrogen, or alkyl$_{1-6}$.

Suitably $R_{22}$ is hydrogen, alkyl$_{1-6}$, aryl, benzyl, heteroaryl, alkyl substituted by halogen or hydroxyl, or phenyl substituted by a member selected from the group consisting of halo, cyano, alkyl$_{1-12}$, alkoxy $_{1-6}$, halosubstituted alkyl$_{1-6}$, alkylthio, alkylsulphonyl, or alkylsulfinyl; or $R_{21}$ and $R_{22}$ may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably $R_f$ is $NR_{21}R_{22}$, and more preferably $R_{21}$ and $R_{22}$ are both hydrogen.

When the $R_2$ cycloalkyl moiety is substituted by $NR_7R_{17}$ group, or $NR_7R_{17}$ $C_{1-10}$ alkyl group, and the $R_7$ and $R_{17}$ are as defined in Formula (I), the substituent is preferably an amino, amino alkyl, or an optionally substitued pyrrolidinyl moiety.

A preferred ring placement on the cycloalkyl moiety is the 4-position, such as in a $C_6$ ring. When the cycloalkyl ring is di-substituted it is preferably di-substituted at the 4 position, such as in:

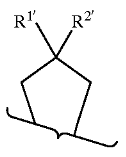

wherein $R^{1'}$ and $R^{2'}$ are independently the optional substitutents indicated above for $R_2$. Preferably, $R^{1'}$ and $R^{2'}$ are hydrogen, hydroxy, alkyl, substituted alkyl, optionally substituted alkyne, aryl, arylalkyl, $NR_7R_{17}$, and $N(R_{10})C(O)R_{11}$. Suitably, alkyl is $C_{1-4}$ alkyl, such as methyl, ethyl, or isopropyl; $NR_7R_{17}$ and $NR_7R_{17}$ alkyl, such as amino, methylamino, aminomethyl, aminoethyl; substituted alkyl such as in cyanomethyl, cyanoethyl, nitroethyl, pyrrolidinyl; aryl such as in phenyl; arylalkyl, such as in benzyl; optionally substituted alkyne, such as ethyne or propynyl; or together $R^{1'}$ and $R^{2'}$ are a keto functionality.

When $R_2$ is $(CR_{10}R_{20})_nNR_{13}R_{14}$, $R_{13}$ and $R_{14}$ are as defined in Formula (I), that is $R_{13}$ and $R_{14}$ are each independently selected from hydrogen, optionally substituted $C_{1-4}$ alkyl, optionally substituted aryl or an optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$. It is recognized that in some instances this can yield the same moiety as a heterocyclic $C_{1-10}$ alkyl moiety noted above which is also a suitable $R_2$ variable. Preferably $R_{13}$ and $R_{14}$ are independently hydrogen, $C_{1-4}$ alkyl, preferably methyl, or benzyl. The n term is preferably 1 to 4, more preferably 3 or 4, and most preferably 3, such as in a propyl group. Preferred groups include, but are not limited to, aminopropyl, (N-methyl-N-benzyl)aminopropyl, (N-Phenylmethyl) amino-1-propyl, or diethylamino propyl.

When $R_2$ is a $(CR_{10}R_{20})_nC(Z)OR_{11}$ group, $R_{11}$ is suitably hydrogen, $C_{1-4}$ alkyl, especially methyl. The n term is preferably 1 to 4, more preferably 2 or 3, such as in an ethyl or propyl group. Preferred groups include, but are not limited to, carboxymethyl-1-butyl, carboxy-1-propyl, or 2-acetoxyethyl.

When $R_2$ is a $(CR_{10}R_{20})_nS(O)_mR_{18}$ group m is 0, 1, or 2, and $R_{18}$ is preferably aryl, especially phenyl, or $C_{1-10}$ alkyl, especially methyl. The n term is preferably 1 to 4, more preferably 2 or 3, such as in an ethyl or propyl group.

When $R_2$ is a $(CR_{10}R_{20})_nOR_{11}$ group, $R_{11}$ is suitably hydrogen, aryl, especially phenyl, or $C_{1-10}$ alkyl, especially methyl or ethyl. The n term is preferably 1 to 4, more preferably 2 or 3, such as in an ethyl or propyl group.

When $R_2$ is a $(CR_{10}R_{20})_nNHS(O)_2R_{18}$ group, $R_{18}$ is suitably alkyl, especially methyl. The n term is preferably 1 to 4, more preferably 2 or 3, such as in an ethyl or propyl group.

When $R_2$ is a optionally substituted aryl, the aryl is preferably phenyl. The aryl ring may be optionally substituted one or more times, preferably by one or two substituents, independently selected from $C_{1-4}$ alkyl, halogen, especially fluoro or chloro, $(CR_{10}R_{20})_tOR_{11}$, $(CR_{10}R_{20})_tNR_{10}R_{20}$, especially amino or mono- or di-alkylamino; $(CR_{10}R_{20})_tS(O)_mR_{18}$, wherein m is 0, 1 or 2; SH—, $(CR_{10}R_{20})_nNR_{13}R_{14}$, $NR_{10}C(Z)R_3$ (such NHCO ($C_{1-10}$ alkyl)); $NR_{10}S(O)_mR_8$ (such as $NHSO_2(C_{1-10}$ alkyl)); and t is 0, or an integer of 1 to 4. Preferably the phenyl is substituted in the 3 or 4-position by $(CR_{10}R_{20})_tS(O)_mR_{18}$, and $R_{18}$ is preferably $C_{1-10}$ alkyl, especially methyl.

When $R_2$ is an optionally substituted heteroaryl or heteroarylalkyl group the ring may be optionally substituted one or more times, preferably by one or two substituents, independently selected from one or more times, by $C_{1-4}$ alkyl, halogen, especially fluoro or chloro, $(CR_{10}R_{20})_tOR_{11}$, $(CR_{10}R_{20})_tNR_{10}R_{20}$, especially amino or mono- or di-alkylamino —$(CR_{10}R_{20})_tS(O)_mR_{18}$, wherein m is 0, 1 or 2; SH, $(CR_{10}R_{20})_n$—$NR_{13}R_{14}$, $NR_{10}C(Z)R_3$ (such NHCO ($C_{1-10}$ alkyl)); $NR_{10}S(O)_mR_8$ (such as $NHSO_2(C_{1-10}$ alkyl)); t is 0, or an integer of 1 to 4.

One skilled in the art would readily recognize that when $R_2$ is a $(CR_{10}R_{20})_nOC(Z)R_{11}$, or $(CR_{10}R_{20})_nOC(Z)NR_{13}R_{14}$ moiety, or any similarly substituted group that n is preferably at least 2 which will allow for the synthesis of stable compounds.

Preferably $R_2$ is a $C_{1-4}$ alkyl (branched and unbranched), especially methyl, methylthio propyl, a methylsulfinyl propyl, an amino propyl, N-methyl-N-benzylamino propyl group, diethylamino propyl, cyclopropyl methyl, morpholinyl butyl, morpholinyl propyl, a morpholinyl ethyl, a piperidine or a substituted piperidine. More preferably $R_2$ is a methyl, isopropyl, butyl, t-butyl, n-propyl, methyithiopropyl, or methylsulfinyl propyl, morpholino propyl, morpholinyl butyl, phenyl substituted by halogen, thioalkyl or sulfinyl alkyl such as a methylthio, methylsulfinyl or methylsulfonyl moiety; piperidinyl, 1-Formyl4-piperidine, 1-benzyl-4-piperidine, 1-methyl4-piperidine, or a 1-ethoxycarbonyl-4-piperidine.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $OR_3$, or for certain $R_2$ moieties.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m alkyl, wherein m is 0, 1 or 2, such as methyl thio, methylsulfinyl or methyl sulfonyl; amino, mono & di-substituted amino, such as in the $NR_7R_{17}$ group; or where the $R_7R_{17}$ may together with the nitrogen to which they are attached cyclize to form a 5 to 7 membered ring which optionally includes an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; $S(O)_m$ alkyl; amino, mono & di-substituted amino, such as in the $NR_7R_{17}$ group; alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo" or "halogens", include the halogens: chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

"sulfinyl"—the oxide S (O) of the corresponding sulfide, the term "thio" refers to the sulfide, and the term "sulfonyl" refers to the fully oxidized S $(O)_2$ moiety.

"aroyl"—a C(O)Ar, wherein Ar is as phenyl, naphthyl, or aryl alkyl derivative such as defined above, such group include but are not limited to benzyl and phenethyl.

"alkanoyl"—a $C(O)C_{1-10}$ alkyl wherein the alkyl is as defined above.

For the purposes herein the "core" 4-pyrimidinyl moiety for $R_1$ or $R_2$ is referred to

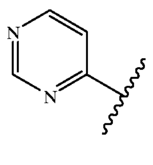

as the formula:

The compounds of the present invention may contain one or more asymmetric carbon atoms and may exist in racemic and optically active forms. All of these compounds are included within the scope of the present invention.

Exemplified compounds of Formula (I) include: 1-(4-Piperidinyl)-4-(4-fluorophenyl)-5-(2-phenoxypyrimidin-4-yl)imidazole 1-(4-piperidinyl)4-(4-fluorophenyl)-5-(2-phenoxy-4-pyridinyl)imidazole 1-(4-piperidinyl)4-(4-fluorophenyl)-5-[2-(4-methoxyphenoxy)-4-pyridinyl] imidazole 1-(4-piperidinyl)4-(4-fluorophenyl)-5-[2-(4-fluorophenoxy)4-pyridinyl]imidazole 1-(Piperidin-4-yl)-4-(4-fluorophenyl)-5-[2-(4-methoxyphenoxy)pyrimidin4-yl] imidazole 1-(Piperidin-4-yl)-4-(4-fluorophenyl)-5-[2-(4-fluorophenoxy)pyrimidin4-yl]-imidazole 1-(Piperidin-4-yl)-4-(4-fluorophenyl)-5-[2-(4-aminocarbonylphenoxy) pyrimidin-4-yl-imidazole 1-(Piperidin-4-yl)-4-(4-fluorophenyl)-5-[2-(4-ethylphenoxy)pyrimidin4-yl] imidazole 1-(Piperidin-4-yl)-4-(4-fluorophenyl)-5-[2-(4-benzyloxyphenoxy)pyrimidin-4-yl]-imidazole 1-(Piperidin-4-yl)-4-(4-fluorophenyl)-5-[2-(4-cyanophenoxy)pyrimidin-4-yl-]imidazole 1-(Piperidin-4-yl)-4-(4-fluorophenyl)-5-[2-(4-hydroxyphenoxy)pyrimidin-4-yl]imidazole 1-(4-hydroxycyclohexyl)-4-(4-fluorophenyl)-5-[2-(phenoxy) pyrimidin-4-yl]imidazole 1-(Piperidin-4-yl)-4-(4-fluorophenyl)-5-[2-(2,6-dimethylphenoxy)pyridin-4-yl] imidazole 1-(Piperidin-4-yl)-4-(4-fluorophenyl)-5-[2-(4-methylphenoxy)pyridin-4-yl]imidazole 1-(Piperidin-4-yl)-4-(4-fluorophenyl)-5-[2-(4-chlorophenoxy)pyridin-4-yl] imidazole 1-[3-(N-Morpholino)propyl]-4-(4-fluorophenyl)-5-[2-(phenoxy)pyrimidin-4-yl]imidazole 1-(Piperidin-4-yl)-4-(4-fluorophenyl)-5-[2-(3-methoxyphenoxy)pyrimidin-4-yl]imidazole 1-(Piperidin-4-yl)-4-(4-fluorophenyl)-5-[2-(4-phenylphenoxy)pyrimidin-4-yl]imidazole 1-(Piperidin-4-yl)-4-(4-fluorophenyl)-5-[2-(4-phenoxyphenoxy)pyrimidin-4-yl]imidazole 1-(Piperidin-4-yl)-4-(4-fluorophenyl)-5-[2-(3 -hydroxyphenoxy)pyrimidin-4-yl]imidazole 1-(3-(N-Morpholino)propyl)-4-(4-fluorophenyl)-5-[2-(4-fluorophenoxy)pyrimidin-4-yl]imidazole 1-(Piperidin-4-yl)-4-(4-fluorophenyl)-5-[2-(2-hydroxyphenoxy)pyrimidin-4-yl]imidazole 1-(Piperidin-4-yl)-4-(4-fluorophenyl)-5-[2-((3,4-methylenedioxy)phenoxy)pyrimidin-4-yl]imidazole 1-(Piperidin-4-yl)-4-(4-fluorophenyl)-5-[2-(3-fluorophenoxy)pyrimidin-4-yl]imidazole 1-(Piperidin-4-yl)-4-(4-fluorophenyl)-5-[2-(2-fluorophenoxy)pyrimidin-4-yl] imidazole 1-(Piperidin-4-yl)4(4-fluorophenyl)-5-[2-(2-methoxyphenoxy)pyrimidin-4-yl]imidazole 1-(Piperidin-4-yl)-4-(4-fluorophenyl)-5-[2-(3-trifluoromethylphenoxy) pyrimidin-4-tl]imidazole 1-(Piperidin-4-yl)4-(4-fluorophenyl)-5-[2-(3,4-difluorophenoxy)pyrimidin-4-yl] imidazole 1-(Piperidin-4-yl)-4-(4-fluorophenyl)-5-[2-(4-methylsulfonylphenoxy)pyrimidin-4-yl]imidazole 1-(4-Piperidinyl)-4-(4-fluorophenyl)-5-(2-thiophenoxypyrimidin-4-yl)imidazole 1-(4-Piperidinyl)-4-(4-fluorophenyl)-5-[2-(1-methyltetrazol-5-ylthio)pyridin-4-yl]imidazole The compounds of Formula (I) may be obtained by applying synthetic procedures, some of which are illustrated in Schemes I to XI herein. The synthesis provided for in these Schemes is applicable for the producing compounds of Formula (I) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. While the schemes describe compounds of Formula (I) with Y as oxygen, one skilled in the art would readily be able to make compounds of Formula (I) wherein Y is sulfur using similar reaction processes as exemplified herein.

Once the imidazole nucleus has been established, further compounds of Formula (I) may be prepared by applying standard techniques for functional group interconversion, well known in the art. For instance: —C(O)$NR_{13}R_{14}$ from —$CO_2CH_3$ by heating with or without catalytic metal cyanide, e.g. NaCN, and $HNR_{13}R_{14}$ in $CH_3OH$; —OC(O)$R_3$ from —OH with e.g., ClC(O)$R_3$ in pyridine; —$NR_{10}$—C(S)$NR_{13}R_{14}$ from —$NHR_{10}$ with an alkylisothiocyante or thiocyanic acid; $NR_6C(O)OR_6$ from —$NHR_6$ with the alkyl chloroformate; —$NR_{10}C(O)NR_{13}R_{14}$ from —$NHR_{10}$ by treatment with an isocyanate, e.g. HN═C═O or $R_{10}$N═C═O; —$NR_{10}$—C(O)$R_8$ from —$NHR_{10}$ by treatment with Cl—C(O)$R_3$ in pyridine; —C(═$NR_{10}$)$NR_{13}R_{14}$ from —C($NR_{13}R_{14}$)$SR_3$ with $H_3NR_3^+OAc^-$ by heating in alcohol; —C($NR_{13}R_{14}$)$SR_3$ from —C(S)$NR_{13}R_{14}$ with $R_6$—I in an inert solvent, e.g. acetone; —C(S)$NR_{13}R_{14}$ (where $R_{13}$ or $R_{14}$ is not hydrogen) from —C(S)$NH_2$ with $HNR_{13}R_{14}$—C(═NCN)—$NR_{13}R_{14}$ from —C(═$NR_{13}R_{14}$)—$SR_3$ with $NH_2CN$ by heating in anhydrous alcohol, alternatively from —C(═NH)—$NR_{13}R_{14}$ by treatment with BrCN and NaOEt in EtOH; —$NR_{10}$—C(═NCN)$SR_8$ from —$NHR_{10}$ by treatment with $(R_8S)_2C$═NCN; —$NR_{10}SO_2R_3$ from —$NHR_{10}$ by treatment with $ClSO_2R_3$ by heating in pyridine; —$NR_{10}C(S)R_3$ from —$NR_{10}C(O)R_8$ by treatment with Lawesson's reagent [2,4bis(4-methoxyphenyl)-1,3,2,4-dithiadiphosphetane-2,4-disulfide]; —$NR_{10}SO_2CF_3$ from —$NHR_6$ with triflic anhydride and base wherein $R_3$, $R_6$, $R_{10}$, $R_{13}$ and $R_{14}$ are as defined in Formula (I) herein.

Precursors of the groups $R_1$, $R_2$ and $R_4$ can be other $R_1$, $R_2$ and $R_4$ groups which can be interconverted by applying standard techniques for functional group interconversion. For example a compound of the formula (I) wherein $R_2$ is halo-substituted $C_{1-10}$ alkyl can be converted to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_{18}S(O)_2X$ wherein X is halo (e.g., chloro) to yield the corresponding $C_{1-10}$alkylNHS(O)$_2R_{18}$ compound.

Alternatively a compound of the formula (I) where $R_2$ is halo-substituted $C_{1-10}$-alkyl can be reacted with an amine $R_{13}R_{14}NH$ to yield the corresponding $C_{1-10}$-alkyl$NR_{13}R_{14}$ compound, or can be reacted with an alkali metal salt of $R_{18}SH$ to yield the corresponding $C_{1-10}$alkyl$SR_{18}$ compound.

SCHEME I

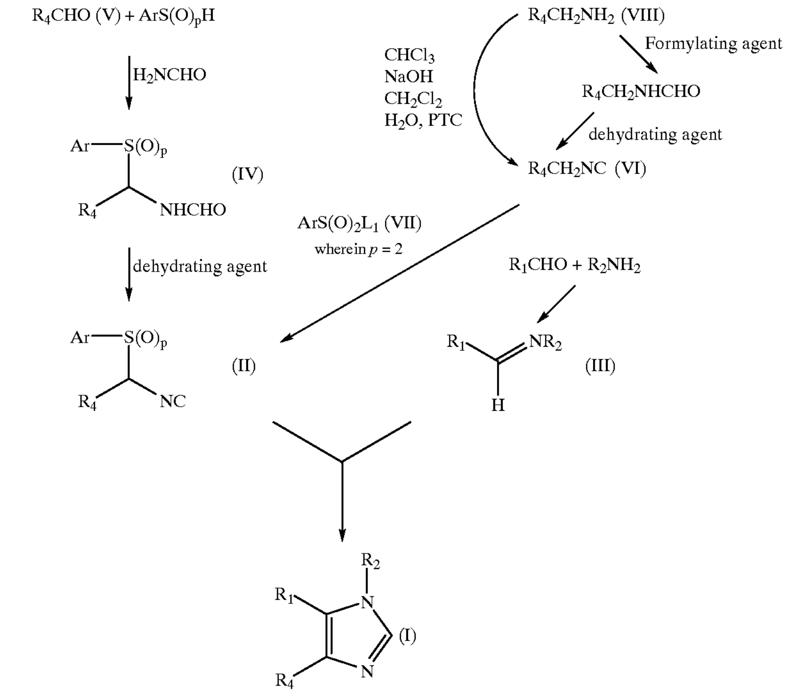

Referring to Scheme I the compounds of Formula (I) are suitably prepared by reacting a compound of the Formula (II) with a compound of the Formula (III) wherein p is 0 or 2, $R_1$, $R_2$ and $R_4$ are as defined herein, for Formula (I), or are precursors of the groups $R_1$, $R_2$ and $R_4$, and Ar is an optionally substituted phenyl group, and thereafter if necessary converting a precursor of $R_1$, $R_2$ and $R_4$ to a group $R_1$, $R_2$ and $R_4$. It is recognized that $R_2$NH2 which is reacted with $R_1$CHO to form the irnine, Formula (III) the $R_2$ moiety when it contains a reactive functional group, such as a primary or secondary amine, an alcohol, or thiol compound the group must be suitably protected. Suitable protecting groups may be found in, Protecting Groups in Organic Synthesis, Greene T W, Wiley-Interscience, New York, 1981, whose disclosure is incorporated herein by reference. For instance, when $R_2$ is a heterocyclic ring, such as a piperidine ring, the nitrogen is protected with groups such as t-Boc, $CO_2R_{18}$, or a substitued arylalkyl moiety.

Suitably, the reaction is performed at ambient temperature or with cooling (e.g. −50° to 10°) or heating in an inert solvent such as methylene chloride, DMF, tetrahydrofuran, toluene, acetonitrile, or dimethoxyethane in the presence of an appropriate base such as $K_2CO_3$, t-bu$NH_2$, 1,8-diazabicyclo [5.4.0.] undec-7-ene (DBU), or a guanidine base such as 1,5,7-triaza-bicyclo [4.4.0] dec-5-ene (TBD). The intermediates of formula (II) have been found to be very stable and capable of storage for a long time. Preferably, p is 2. PTC is defined as a phase transfer catalyst for use herein.

Compounds of the Formula (II) have the structure:

(II)

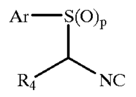

wherein p is 0, or 2; $R_4$ is as defi ned for Formula (I) and Ar is an optionally substituted aryl as defined herein. Suitably, Ar is phenyl optionally substituted by $C_{1-4}$alkyl, $C_{1-4}$ alkoxy or halo. Preferably Ar is phenyl or 4-methylphenyl, i.e. a tosyl derivative.

Reaction a compound of the Formula (II) wherein p=2, with a compound of the Formula (III)—Scheme I gives consistently higher yields of compounds of Formula (I) than when p=0. In addition, the reaction of Formula (II) compounds wherein p=2 is more environmentally and economically attractive. When p=0, the preferred solvent used is methylene chloride, which is environmentally unattractive for large scale processing, and the preferred base, TBD, is also expensive, and produces some byproducts and impurities, than when using the commercially attractive synthesis (p=2) as further described herein.

As noted, Scheme I utilizes the 1,3-dipolar cycloadditions of an anion of a substituted aryl thiomethylisocyanide (when p=0) to an imine. More specifically, this reaction requires a strong base, such as an amine base, to be used for the deprotonation step. The commercially available TBD is preferred although t-butoxide, Li+ or Na+, or K+ hexamethyldisilazide may also be used. While methylene chloride is the prefered solvent, other halogenated solvents, such as chloroform or carbon tetrachloride; ethers, such as THF, DME, DMF, diethylether, t-butyl methyl ether; as well as acetonitrile, toluene or mixtures thereof can be utiltized. The reaction may take place from about −20° C. to about; 40° C., preferably from about 0° C. to about 23° C., more preferably from about 0° C. to about 10° C., and most preferably about 4° C. for reactions involving an $R_1$ group of pyrimidine. For compounds wherein $R_1$ is pyridine, it is recognized that varying the reations conditions of both temperature and solvent may be necessary, such as decreasing temperatures to about −50° C. or changing the solvent to THF.

In a further process, compounds of Formula (I) may be prepared by coupling a suitable derivative of a compound of Formula (IX):

(IX)

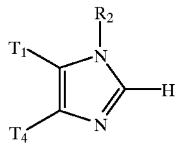

wherein $T_1$ is hydrogen and $T_4$ is $R_4$, or alternatively $T_1$ is $R_1$ and $T_4$ is H in which $R_1$, $R_2$ and $R_4$ are as hereinbefore defined; with: (i) when $T_1$ is hydrogen, a suitable derivative of the heteroaryl ring $R_1H$, under ring coupling conditions, to effect coupling of the heteroaryl ring $R_1$ to the irnidazole nucleus at position 5; (ii) when $T_4$ is hydrogen, a suitable derivative of the aryl ring $R_4H$, under ring coupling conditions, to effect coupling of the aryl ring $R_4$ to the imidazole nucleus at position 4.

Such aryl/heteroaryl coupling reactions are well known to those skilled in the art. In general, an organometallic synthetic equivalent of an anion of one component is coupled with a reactive derivative of the second component, in the presence of a suitable catalyst. The anion equivalent may be formed from either the imidazole of Formula (IX), in which case the aryl/heteroaryl compound provides the reactive derivative, or the aryl/heteroaryl compound in which case the imidazole provides the reactive derivative. Accordingly, suitable derivatives of the compound of Formula (IX) or the aryl/heteroaryl rings include organometallic derivatives such as organomagnesium, organozinc, organostannane and boronic acid derivatives and suitable reactive derivatives include the bromo, iodo, fluorosulfonate and trifluoromethanesulphonate derivatives. Suitable procedures are described in WO 91/19497, the disclosure of which is incorporated by reference herein.

Suitable organomagnesium and organozinc derivatives of a compound of Formula (IX) may be reacted with a halogen, fluorosulfonate or triflate derivative of the heteroaryl or aryl ring, in the presence of a ring coupling catalyst, such as a palladium (O) or palladium (II) catalyst, following the procedure of Kumada et al., Tetrahedron Letters, 22, 5319 (1981). Suitable such catalysts include tetrakis-(triphenylphosphine)palladium and $PdCl_2$[1,4-bis-(diphenylphosphino)-butane], optionally in the presence of lithium chloride and a base, such as triethylamine. In addition, a nickel (II) catalyst, such as $Ni(II)Cl_2$(1,2-biphenylphosphino)ethane, may also be used for coupling an aryl ring, following the procedure of Pridgen et al., J. Org. Chem, 1982, 47, 4319. Suitable reaction solvents include hexamethylphosphor-amide. When the heteroaryl ring is 4-pyridyl, suitable derivatives include 4-bromo- and 4-iodo-pyridine and the fluorosulfonate and triflate esters of 4-hydroxy pyridine. Similarly, suitable derivatives for when the aryl ring is phenyl include the bromo, fluorosulfonate, triflate and, preferably, the iodo-derivatives. Suitable organomagnesium and organozinc derivatives may be obtained by treating a compound of Formula (IX) or the bromo derivative thereof with an alkyllithium compound to yield the corresponding lithium reagent by deprotonation or transmetallation, respectively. This lithium intermediate may then be treated with an excess of a magnesium halide or zinc halide to yield the corresponding organometallic reagent.

A trialkyltin derivative of the compound of Formula (IX) may be treated with a bromide, fluorosulfonate, triflate, or, preferably, iodide derivative of an aryl or heteroaryl ring compound, in an inert solvent such as tetrahydrofuran, preferably containing 10% hexamethylphosphoramide, in the presence of a suitable coupling catalyst, such as a palladium (O) catalyst, for instance tetrakis-(triphenylphosphine)-palladium, by the method described in by Stille, J. Amer. Chem. Soc, 1987, 109. 5478, U.S. Pat. Nos. 4,719,218 and 5,002,942, or by using a palladium (II) catalyst in the presence of lithium chloride optionally with an added base such as triethylamine, in an inert solvent such as dimethyl formamide. Trialkyltin derivatives may be conveniently obtained by metallation of the corresponding compound of Formula (IX) with a lithiating agent, such as s-butyl-lithium or n-butyllithium, in an ethereal solvent, such as tetrahydrofuran, or treatment of the bromo derivative of the corresponding compound of Formula (IX) with an alkyl lithium, followed, in each case, by treatment with a trialkyltin halide. Alternatively, the bromo-derivative of a compound of Formula (IX) may be treated with a suitable heteroaryl or aryl trialkyl tin compound in the presence of a catalyst such as tetrakis-(triphenyl-phosphine)-palladium, under conditions similar to those described above.

Boronic acid derivatives are also useful. Hence, a suitable derivative of a compound of Formula (IX), such as the bromo, iodo, triflate or fluorosulphonate derivative, may be reacted with a heteroaryl- or aryl-boronic acid, in the presence of a palladium catalyst such as tetrakis-(triphenylphosphine)-palladium or $PdCl_2$[1,4bis-(diphenyl-phosphino)-butane] in the presence of a base such as sodium bicarbonate, under reflux conditions, in a solvent such as dimethoxyethane (see Fischer and Haviniga, Rec. Trav. Chim. Pays Bas, 84, 439, 1965, Snieckus, V., Tetrahedron Lett., 29, 2135, 1988 and Terashimia, M., Chem. Pharm. Bull., 11, 4755, 1985). Non-aqueous conditions, for instance, a solvent such as DMF, at a temperature of about 100° C., in the presence of a Pd(II) catalyst may also be employed (see Thompson W J et al, J Org Chem, 49, 5237, 1984). Suitable boronic acid derivatives may be prepared by treating the magnesium or lithium derivative with a trialkylborate ester, such as triethyl, tri-iso-propyl or tributylborate, according to standard procedures.

In such coupling reactions, it will be readily appreciated that due regard must be exercised with respect to functional groups present in the compounds of Formula (IX). Thus, in general, amino and sulfur substituents should be non-oxidised or protected.

Compounds of Formula (IX) are imidazoles and may be obtained by any of the procedures herein before described for preparing compounds of Formula (I). In particular, an α-halo-ketone or other suitably activated ketones $R_4COCH_2Hal$ (for compounds of Formula (IX) in which $T_1$ is hydrogen) or $R_1COCH_2Hal$ (for compounds of Formula (IX) in which $T_4$ is hydrogen) may be reacted with an amidine of the formula $R_2NH—C═NH$, wherein $R_2$ is as defined in Formula (I), or a salt thereof, in an inert solvent such as a halogenated hydrocarbon solvent, for instance chloroform, at a moderately elevated temperature, and, if necessary, in the presence of a suitable condensation agent such as a base. The preparation of suitable a-halo-ketones is described in WO 91/19497. Suitable reactive esters include esters of strong organic acids such as a lower alkane sulphonic or aryl sulphonic acid, for instance, methane or p-toluene sulphonic acid. The amidine is preferably used as the salt, suitably the hydrochloride salt, which may then be converted into the free amidine in situ, by employing a two phase system in which the reactive ester is in an inert organic solvent such as chloroform, and the salt is in an aqueous phase to which a solution of an aqueous base is slowly added, in dimolar amount, with vigorous stirring. Suitable amidines may be obtained by standard methods, see for instance, Garigipati R, Tetrahedron Letters, 190, 31, 1989.

Compounds of Formula (I) may also be prepared by a process which comprises reacting a compound of Formula (IX), wherein $T_1$ is hydrogen, with an N-acyl heteroaryl salt, according to the method disclosed in U.S. Pat. No. 4,803, 279, U.S. Pat. No. 4,719,218 and U.S. Pat. No. 5,002,942, to give an intermediate in which the heteroaryl ring is attached to the imidazole nucleus and is present as a 1,4-dihydro derivative thereof, which intermediate may then be subjected to oxidative-deacylation conditions (Scheme II). The heteroaryl salt, for instance a pyridinium salt, may be either preformed or, more preferably, prepared in situ by adding a substituted carbonyl halide (such as an acyl halide, an aroyl halide, an arylalkyl haloformate ester, or, preferably, an alkyl haloformate ester, such as acetyl bromide, benzoylchloride, benzyl chloroformate, or, preferably, ethyl chloroformate) to a solution of the compound of Formula (IX) in the heteroaryl compound $R_1H$ or in an inert solvent such as methylene chloride to which the heteroaryl compound has been added. Suitable deacylating and oxidising conditions are described in U.S. Pat. Nos. 4,803,279, 4,719,218 and 5,002,942, which references are hereby incorporated by reference in their entirety. Suitable oxidizing systems include sulfur in an inert solvent or solvent mixture, such as decalin, decalin and diglyme, p-cymene, xylene or mesitylene, under reflux conditions, or, preferably, potassium t-butoxide in t-butanol with dry air or oxygen.

SCHEME II

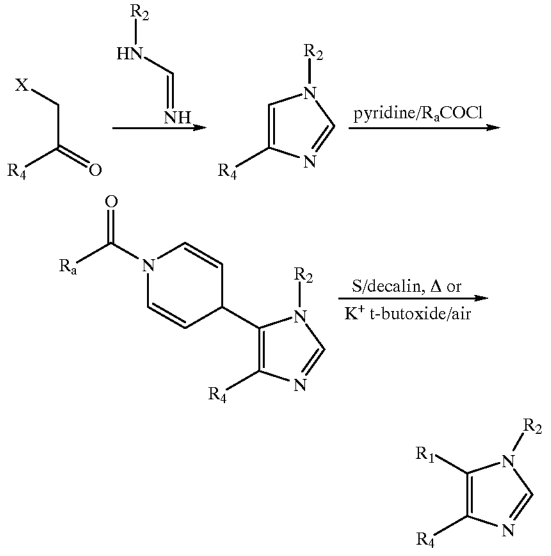

In a further process, illustrated in Scheme III below, compounds of Formula (I) may be prepared by treating a compound of Formula (X) thermally or with the aid of a cyclising agent such as phosphorus oxychloride or phosphorus pentachloride (see Engel and Steglich, Liebigs Ann Chem, 1978, 1916 and Strzybny et al., J Org Chem, 1963, 28, 3381). Compounds of Formula (X) may be obtained, for instance, by acylating the corresponding a-keto-amine with an activated formate derivative such as the corresponding anhydride, under standard acylating conditions followed by formation of the imine with $R_2NH_2$. The aminoketone may be derived from the parent ketone by oxamination and reduction and the requisite ketone may in turn be prepared by decarboxylation of the beta-ketoester obtained from the condensation of an aryl (heteroaryl) acetic ester with the $R_1COX$ component.

SCHEME III

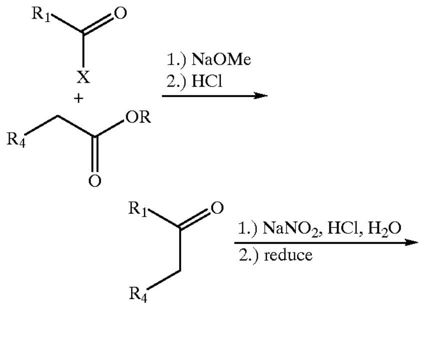

-continued

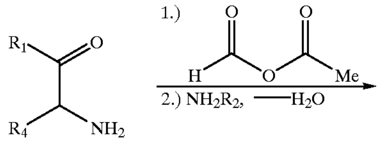

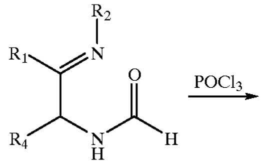

formula (X)

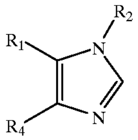

In Scheme IV illustrated below, two (2) different routes which use ketone (formula XI) for preparing a compound of Formula (I). A heterocyclic ketone (XI) is prepared by adding the anion of the alkyl heterocycle such as 4-methyl-quinoline (prepared by treatment thereof with an alkyl lithium, such as n-butyl lithium) to an N-alkyl-O-alkoxybenzamide, ester, or any other suitably activated derivative of the same oxidation state. Alternatively, the anion may be condensed with a benzaldehyde, to give an alcohol which is then oxidised to the ketone (XI).

(b) an excess of an acyl halide, for instance an acyl chloride, of the Formula (XIV):

$R_4COHal$ (XIV)

wherein $R_4$ is as hereinbefore defmed and Hal is halogen, or a corresponding anhydride, to give a bis-acylated intermediate which is then treated with a source of ammonia, such as ammonium acetate.

SCHEME V

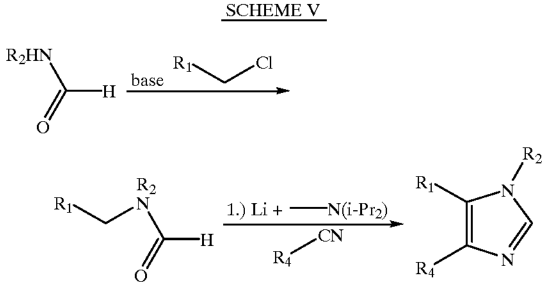

(XII)

One variation of this approach is illustrated in Scheme V above. A primary amine ($R_2NH_2$) is treated with a halomethyl heterocycle of Formula $R_1CH_2X$ to give the secondary amine which is then converted to the amide by standard techniques. Alternatively the amide may be prepared as illustrated in scheme V by alkylation of the formamide with $R_1CH_2X$. Deprotonation of this amide with a strong amide base, such as lithium di-iso-propyl amide or sodium bis-(trimethylsilyl)amide, followed by addition of an excess of an aroyl chloride yields the bis-acylated compound which is then closed to an imidazole compound of Formula (I), by heating in acetic acid containing ammonium acetate.

SCHEME IV

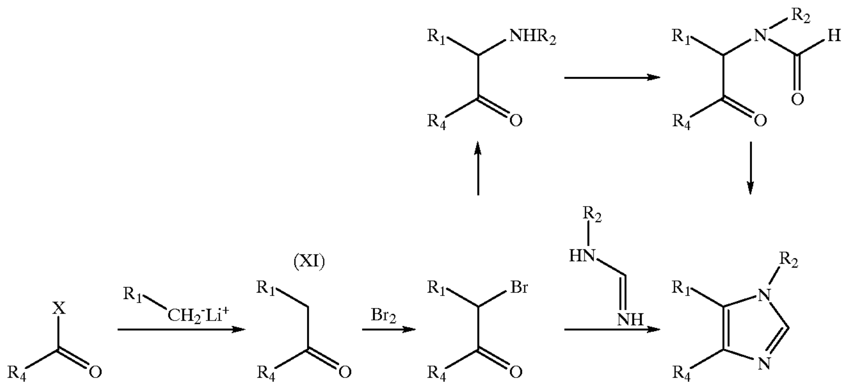

In a further process, N-substituted compounds of Formula (I) may be prepared by treating the anion of an amide of Formula (XII):

$R_1CH_2NR_2COH$ (XII)

wherein $R_1$ and $R_2$ with:

(a) a nitrile of the Formula (XIII):

R4CN (XIII)

wherein $R_4$ is as hereinbefore defined, or

Alternatively, the anion of the amide may be reacted with a substituted aryl nitrile to produce the imidazole of Formula (I) directly.

The following description and schemes are further exemplification of the process as previously described above in Scheme I. Various pyrimidine aldehyde derivatives 6, as depicted in scheme VI below, can be prepared by modification of the procedures of Bredereck et al. (*Chem. Ber.* 1964, 97, 3407) whose disclosure is incorporated by reference herein. These pyrirnidine aldehydes are then utilized as intermediates in the synthesis as further described herein.

SCHEME VI

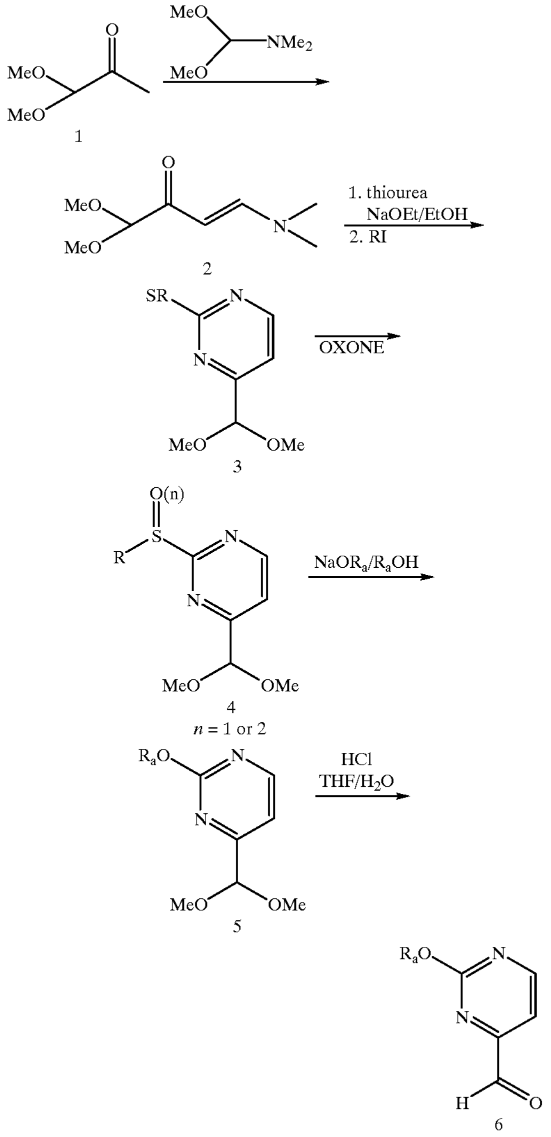

The reaction of imines with tosylmethyl isonitriles was first reported by van Leusen (van Leusen, et al., *J. Org. Chem.* 1977, 42, 1153.) Reported were the following conditions: tert butyl amine($tBuNH_2$) in dimethoxyethane (DME), $K_2CO_3$ in MeOH, and NaH in DME. Upon re-examination of these conditions each was found produce low yields. A second pathway involving amine exchange to produce the t-butyl imine followed by reaction with the isocyanide to produce a 1-tBu imidazole was also operating. This will likely occur using any primary amine as a base. The secondary amines, while not preferred may be used, but may also decompose the isonitrile slowly. Reactions will likely require about 3 equivalents of amine to go to completion, resulting in approximately 50% isolated yields. Hindered secondary amines (diisopropylamine) while usable are very slow and generally not too effective. Use of tertiary and aromatic amines, such as pyridine, and triethylamine gave no reaction under certain test conditions, but more basic types such as DBU, and 4-dimethylamino pyridine (DMAP) while slow, did produce some yields and hence may be suitable for use herein.

As depicted in Schemes VII and VIII below, the pyrimidine aldehydes of Scheme VI, can be condensed with a primary amine, to generate an imine, which may suitably be isolated or reacted in situ, with the desired isonitrile in the presence of a variety of suitable bases, and solvents as described herein to afford the 5-(4-pyrimidinyl)-substituted imidazoles, wherein $R_2$ and $R_4$ are as defined herein for Formula (I) compounds.

One preferred method for preparing compounds of Formula (I) is shown below in Scheme VII. The imines, prepared and isolated in a separate step were often tars, which were hard to handle. The black color was also often carried over into the final product. The yield for making the imines varied, and environmentally less-acceptable solvents, such as $CH_2Cl_2$ were often used in their preparation.

This reaction, wherein p=2, requires a suitable base for the reaction to proceed. The reaction requires a base strong enough to deprotonate the isonitrile. Suitable bases include an amine, a carbonate, a hydride, or an alkyl or aryl lithium reagent; or mixtures thereof. Bases include, but are not limited to, potassium carbonate, sodium carbonate, primary and secondary amines, such as t-butylamine, diisopropyl amine, morpholine, piperidine, pyrrolidine, and other non-nucleophilic bases, such as DBU, DMAP and 1,4-diazabicyclo[2.2.2]octane (DABCO).

Suitable solvents for use herein, include but are not limited to N,N-dimethyl-formamide (DMF), MeCN, halogenated solvents, such as methylene chloride or chloroform, tetrahydrofuran (THF), dimethylsulfoxide (DMSO), alcohols, such as methanol or ethanol, benzene, or toluene, DME or EtOAc. Preferably the solvent is DMF, DME, THF, or MeCN, more preferably DMF. Product isolation may generally be accomplished by adding water and filtering the product as a clean compound.

SCHEME VII

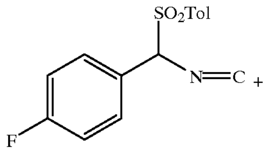

1

-continued

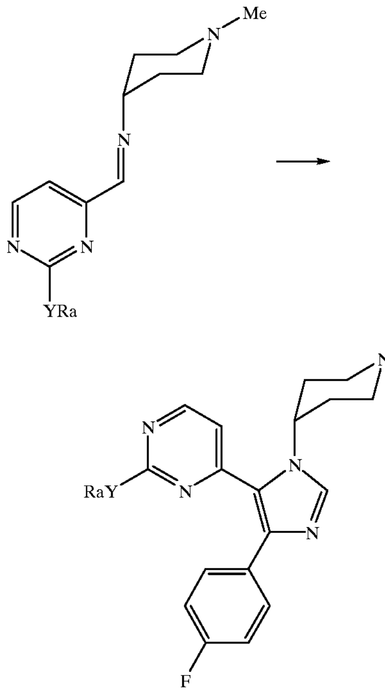

While not convenient for large scale work, addition of NaH to the isonitrile, perhaps with temperatures lower than 25° C. (in THF) are likely needed. Additionally, BuLi has also been reported to be an effective base for deprotonating tosyl benzylisonitriles at −50° C. (DiSanto, et al., *Synth. Commun.* 1995, 25, 795).

Various temperature conditions may be utilized depending upon the preferred base. For instance, $tBuNH_2$/DME, $K_2CO_3$/MeOH, $K_2CO_3$ in DMF, at temperatures above 40° C., the yields may drop to about 20% but little difference is expected between 0° C. and 25° C. Consequently, temperature ranges below 0° C., and above 80° C. are contemplated as also being within the scope of this invention. Preferably, the temperature ranges are from about 0° C. to about 25° C. For purposes herein, room temperature, is generally depicted as 25° C., but it is recognized that this may vary from 20° C. to 30° C.

As shown in Scheme VIII below, the imnine is preferably formed in situ in a solvent. This preferred synthesis, is a process which occurs as a one-pot synthesis. Suitably, when the primary amine is utilized as a salt, such as in the dihydrochloride salt in the Examples, the reaction may further include a base, such as potassium carbonate prior to the addition of the isonitrile. Alternatively, the piperidine nitrogen may be required to be protected (PG) as shown below, suitably the PG is BOC or $C(O)_2R$, wherein R is preferably alkyl, aryl, arylalkyl moieties well known to those skilled in the art. Reaction conditions, such as solvents, bases, temperatures, etc. are similar to those illustrated and discussed above for the isolated imine as shown in Scheme VII. One skilled in the art would readily recognize that under some circumstances, the in situ formation of the imine may require dehydrating conditions, or may require acid catalysis.

SCHEME VIII

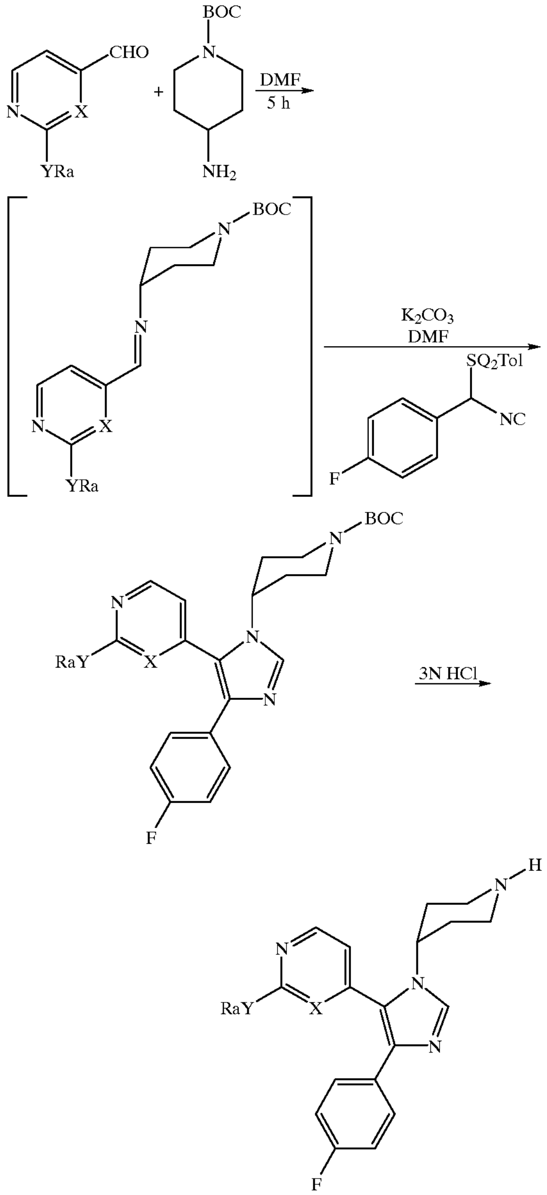

X = CH, N

Scheme IX, describes an alternative process for making compounds of formula (I). In this particular instance, the alkyllthio moiety is oxidized to the methyl sulfinyl or sulfonyl moiety which is reacted with a suitable $YR_a$ moiety.

Scheme IX

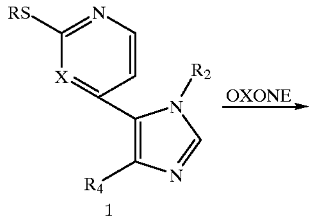

1

-continued

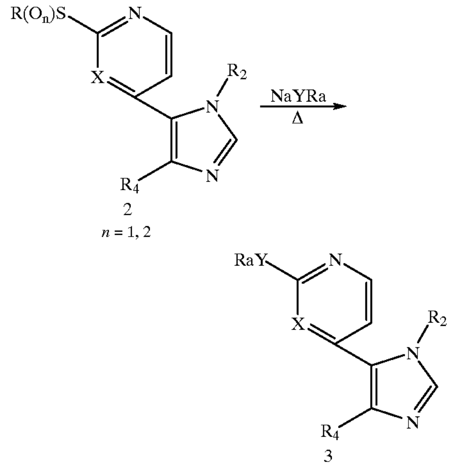

2
n = 1, 2

3

X = CH, N; Y = O, S

Another embodiment of the present invention is the novel hydrolysis of 2-thiomethylpyrimidine acetal to 2-thiomethylpyrimidine aldehyde, as shown in Scheme X below. Hydrolysis of the acetal to aldehyde using various known reaction conditions, such as formic acid, did not produce a satisfactory yield of the aldehyde, <13%) was obtained. The preferred synthesis involves the use of AcOH (fresh) as solvent and concentrated $H_2SO_4$ under heating conditions, preferably a catalytic amount of sulfuric acid. Heating conditions include temperatures from about 60 to 85° C., preferably from about 70 to about 80° C. as higher temperatures show a darkening of the reaction mixture. After the reaction is completeed the mixture is cooled to about room temperature and the acetic acid is removed. A more preferred alternative procedure to this involves heating the acetal in 3N HCl at 40° C. for about 18 hours, cooling and extracting the bicarbonate neutralized solution into EtOAc Scheme X

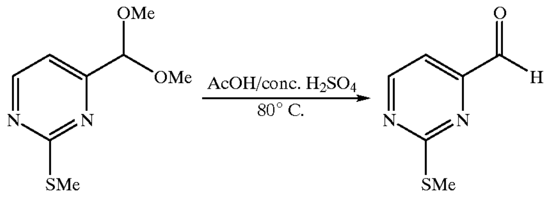

The final 2-(RaY)pyrimidin4-yl imidazole compounds of Formula (I), as well as similar pyridine containing compounds can be prepared by one of three methods: 1) direct reaction of the 2-(RaY)pyrimidine imine with the isonitrile; 2) oxidation of the 2-alkylthiopyrimidine derivative to the corresponding sulfoxide followed by displacement with the desired HYRa under basic conditions, for example using a metal salt of HYRa or in the presence of a non-nucleophilic amine or alkali metal base; or 3) reaction of the 2-halopyrimidine or pyridine imine with the isonitrile followed by displacement with HYRa under basic conditions described in the second method, see also Adams et al., U.S. Ser. No. 08/659,102 filed Jun. 3, 1996, Scheme XI, whose disclosure is incorporated herein by reference in its entirety.

While these schemes herein are presented, for instance, with an optionally substituted piperidine moiety for the resultant $R_2$ position, or a 4-fluoro phenyl for $R_4$, any suitable $R_2$ moiety or $R_4$ moiety may be added in this manner if it can be prepared on the primary amine. Similarly, any suitable $R_4$ can be added via the isonitrile route.

The compounds of Formula (II), in Scheme I, may be prepared by the methods of van Leusen et al., supra. For example a compound of the Formula (II) may be prepared by dehydrating a compound of the Formula (IV)-Scheme I, wherein Ar, $R_4$ and p are as defined herein.

Suitable dehydrating agents include phosphorus oxychloride, oxalyl chloride, thionyl chloride, phosgene, or tosyl chloride in the presence of a suitable base such as triethylamine or diisopropylethylamine, or similar bases, etc. such as pyridine. Suitable solvents are dimethoxy ether, tetrahydrofuran, or halogenated solvents, preferably THF. The reaction is most efficient when the reaction temperatures are kept between −10° C. and 0° C. At lower temperatures incomplete reaction occurs and at higher temperatures, the solution turns dark and the product yield drops.

The compounds of formula (IV)-Scheme I may be prepared by reacting a compound of the formula (V)-Scheme I, $R_4CHO$ where $R_4$ is as defined herein, with $ArS(O)_pH$ and formamide with or without water removal, preferably under dehydrating conditions, at ambient or elevated temperature e.g. 30° to 150°, conveniently at reflux, optionally in the presence of an acid catalyst. Alternatively trimethysilylchloride can be used in place of the acid catalyst. Examples of acid catalysts include camphor-10-sulphonic acid, formic acid, p-toluenesulphonic acid, hydrogen chloride or sulphuric acid.

An optimal method of making an isonitrile of Formula (II) is illustrated below, in Scheme XI.

SCHEME XI

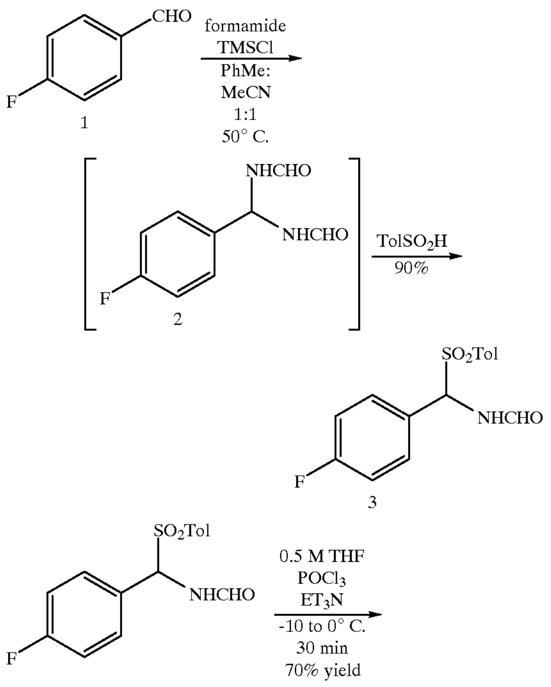

1

2

3

-continued

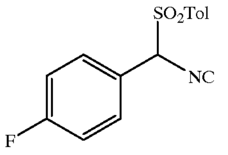

4

The conversion of the substituted aldehyde to the tosylbenzyl formamide may be accomplished by heating the aldehyde, 1—Scheme XI, with an acid, such as p-toluenesulfonic acid, formic acid or camphorsulfonic acid; with formamide and p-toluene-sulfinic acid [under reaction conditions of about 60° C. for about 24 hours]. Preferably, no solvent is used. The reaction, may give poor yields (<30%) when solvents, such as DMF, DMSO, toluene, acetonitrile, or excess formamide are used. Temperatures less than 60° C. are generally poor at producing the desired product, and temperatures in excess of 60° C. may produce a product which decomposes, or obtain a benzylic bis-formamide, 2-Scheme XI.

Another embodiment of the present invention is the synthesis of the tosyl benzyl formamide compound, achieved by reacting the bisformamide intermediate, 2-Scheme XI with p-toluenesulfinic acid. In this preferred route, preparation of the bis-formamide from the aldehyde is accomplished by heating the aldehyde with formamide, in a suitable solvent with acid catalysis. Suitable solvents are toluene, acetonitrile, DMF, and DMSO or mixtures thereof. Acid catalysts, are those well known in the art, and include but are not limited to hydrogen chloride, p-toluenesulfonic acid, camphorsulfonic acid, and other anhydrous acids. The reaction can be conducted at temperatures ranging from about 25° C. to 110° C., preferably about 50° C., suitably for about 4 to about 5 hours, longer reaction times are also acceptable. Product decomposition and lower yields may be observed at higher temperatures (>70° C.) at prolonged reactions times. Complete conversion of the product generally requires water removal from the reaction mixture.

Preferred conditions for converting a bis-formamide derivative to the tosyl benzyl formamide are accomplished by heating the bisformamide in a suitable solvent with an acid catalyst and p-toluenesulfinic acid. Solvents for use in this reaction include but are not limited to toluene, and acetonitrile or mixtures thereof. Additional mixtures of these solvents with DMF, or DMSO may also be used but may result in lower yields. Temperatures may range from about 30° C. to about 100° C. Temperatures lower than 40° C. and higher than 60° C. are not preferred as the yield and rate decreases. Preferably the range is from about 40 to 60° C., most preferably about 50° C. The optimal time is about 4 to 5 hours, although it may be longer. Preferably, acids used include but are not limited to, toluenesulfonic acid, camphorsulfonic acid, and hydrogen chloride and other anhydrous acids. Most preferably the bisformamide is heated in toluene:acetonitrile in a 1:1 ratio, with p-toluenesulfinic acid and hydrogen chloride.

Another embodiment of the present invention is the preferred synthetic route for synthesis of the tosylbenzyl formamide compound which is accomplished using a one-pot procedure. This process first converts the aldehyde to the bis-formamide derivative and subsequently reacts the bis-formnamide derivative with toluenesulfinic acid. This procedure combines the optimized conditions into a single, efficient process. High yields, >90% of the aryl benzylformamide may be obtained in such a manner.

Preferred reaction conditions employ a catalyst, such as trimethylsilyl chloride (TMSCI), in a preferred solvent, toluene:acetonitrile, preferably in a 1:1 ratio. A reagent, such as TMSCl, is preferred which reacts with water produced therein and at the same time produces hydrogen chloride to catalyze the reaction. Also preferred is use of hydrogen chloride and p-toluenesulfonic acid. Therefore, three suitable reaction conditions for use herein include 1) use of a dehydrating agent which also provides hydrogen chloride, such as TMSCl; or by 2) use of a suitable dehydrating agent and a suitable source of acid source, such as but not limited to, camphorsulfonic acid, hydrogen chloride or toluenesulfonic acid; and 3) alternative dehydrating conditions, such as the azeotropic removal of water, and using an acid catalyst and p-toluene sulfinic acid.

Compounds of the formula (II) where p is 2 may also be prepared by reacting in the presence of a strong base a compound of the formula (VI)-Scheme I, $R_4CH_2NC$ with a compound of the formula (VII)-Scheme I, $ArSO_2L_1$ wherein $R_4$ and Ar are as defined herein and $L_1$ is a leaving group such as halo, e.g. fluoro. Suitable strong bases include, but are not limited to, alkyl lithiums such as butyl lithium or lithium diisopropylamide (Van Leusen et al., *Tetrahedron Letters, No.* 23, 2367–68 (1972)).

The compounds of formula (VI)-Scheme I may be prepared by reacting a compound of the formula (VIII)-Scheme I, $R_4CH_2NH_2$ with an alkyl formate (e.g. ethylformate) to yield an intermediate amide which can be converted to the desired isonitrile by reacting with well known dehydrating agent, such as but not limited to oxalyl chloride, phosphorus oxychloride or tosyl chloride in the presence of a suitable base such as triethylamine.

Alternatively a compound of the formula (VIII)-Scheme I may be converted to a compound of the formula (VI)-Scheme I by reaction with chloroform and sodium hydroxide in aqueous dichloromethane under phase transfer catalysis.

The compounds of the formula (III)-Scheme I may be prepared by reacting a compound of the formula $R_1CHO$ with a primary amine $R_2NH_2$.

The amino compounds of the formula (VIII)-Scheme I are known or can be prepared from the corresponding alcohols, oximes or amides using standard functional group interconversions.

Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})n$. Suitable examples of imidazole nitrogen protecting groups include tetrahydropyranyl.

Pharmaceutically acid addition salts of compounds of Formula (I) may be obtained in known manner, for example by treatment thereof with an appropriate amount of acid in the presence of a suitable solvent.

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

Compounds of Formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflanmmatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP).

Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, L-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (L-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation andfor maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories recently. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), (II) and (A), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, thrombosis, glomerulonephritis, diabetes and pancreatic β cells, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994) in vitro. *Bone* 15, 533–538; Lee et al., (1993). B *Ann. N. Y Acad. Sci.* 696, 149–170.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the Formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0. 1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid Formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The Formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100_C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol Formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by the following in vitro assays:

Interleukin-1 (IL-1)

Human peripheral blood monocyres are isolated and purified from either fresh blood preparations from volunteer donors, or from blood bank buffy coats, according to the procedure of Colotta et al, *J Immunol,* 132, 936 (1984). These monocytes ($1\times10^6$) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL4) to secrete IL-2, in concert with A23187 ionophore) or the method of Lee et al., J. Immuno Therapy, 6 (1), 1–12 (1990) (ELISA assay).

Tumour Necrosis Factor (TNF)

Human peripheral blood monocytes are isolated and purified from either blood bank buffy coats or plateletpheresis residues, according to the procedure of Colotta, R. et al., J Immunol, 132(2), 936 (1984). The monocytes are plated at a density of $1\times10^6$ cells/ml mediumn/well in 24-well multidishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds are solubilized in dimethyl sulfoxide/ethanol, such that the final solvent concentration in the culture medium is 0.5% dimethyl sulfoxide/0.5% ethanol). Bacterial lipopoly-saccharide (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., J Immunol, 1991, 147, 4307.

IL-1 and TNF inhibitory activity does not seem to correlate with the property of the compounds of Formula (I) in mediating arachidonic acid metabolism inhibition. Further the ability to inhibit production of prostaglandin and/or leukotriene synthesis, by nonsteroidal anti-inflammatory drugs with potent cyclooxygenase and/or lipoxygenase inhibitory activity does not mean that the compound will necessarily also inhibit TNF or IL-1 production, at non-toxic doses.

In vivo TNF Assay

While the above indicated assay in an in vitro assay, the compounds of Formula (I) may also be tested in an in vivo system such as described in:

(1) "Differentiation In Vivo of Classical Non-Steroidal Antiinflamrnmatory Drugs from Cytokine Suppressive Antiinflammatory Drugs and Other Pharmacological Classes Using Mouse Tumour Necrosis Factor Alpha Production", Griswold et al., *Drugs Under Exp. and Clinical Res., XIX* (6), 243–248 (1993); or in (2) Boehm, et al., 1-substituted 4-aryl-5-pyridinylimidazoles—a new class of cytokine suppressive drugs with low 5-lipoxygenase and cyclooxygenase inhibitory potency. *Journal Of Medicinal Chemistry* 39, 3929–3937 (1996) whose disclosures are incorporated by reference herein in their entirety.

Using the assay described above, representative compounds of Formula (I), Examples 1 to 6, 11, 12, 16, 17, 20 to 24, 26, and 31 demonstrated positive inhibitory activity of <5 uM in this assay.

Interleukin -8 (IL-8)

Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 $\mu$l) into gelating coated 96-well plates. Prior to use, culture medium are replaced with fresh medium (200 $\mu$l). Buffer or test compound (25 $\mu$l, at concentrations between 1 and 10 $\mu$M) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an L-8 ELISA kit obtained from R&D Systems (Minneapolis, Minn.). All data is presented as mean value (ng/ml) of multiple samples based on the standard curve. $IC_{50}$'s where appropriate are generated by non-linear regression analysis.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP. 1 cells and a radiolabeled compound. Patent application U.S. Ser. No. 08/123175 Lee et al., filed September 1993, U.S. Ser. No.; Lee et al., PCT 94/10529 filed Sep. 16, 1994 and Lee et al., *Nature* 300, n(72), 739–746 (December 1994) whose disclosures are incorporated by reference herein in its entirety describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the creening protocol. Regardless of the form of the binding protein, a plurality of compounds are contacted with the binding protein under conditions sufficient to form a compound/binding protein complex and compound capable of forming, enhancing or interfering with said complexes are detected.

Representative final compounds of Formula (I), Examples 1 to 6, 11, 17, 20 to to 31 have all demonstrated positive inhibitory activity of <50 uM in this binding assay.

CSBP KINASE ASSAY

This assay measures the CSBP-catalyzed transfer of $^{32}p$ from [a-$^{32}$P]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, to be published 1996).

Kinase reactions (total volume 30 ul) contain: 25 rnM Hepes buffer, pH 7.5; 10 mM $MgCl_2$; 170 uM ATP(1); 10 uM Na ortho vanadate; 0.4 mM T669 peptide; and 20–80 ng of yeast-expressed purified CSBP2 (see Lee et al., *Nature* 300, n(72), 739–746 (December 1994)). Compounds (5 ul from [6X] stock(2)) are pre-incubated with the enzyme and peptide for 20 min on ice prior to starting the reactions with 32P/MgATP. Reactions are incubated at 30° C. for 10 min and stopped by adding 10 ul of 0.3 M phosphoric acid. 32P-labeled peptide is separated on phosphocellulose (Wattman, p81) filters by spotting 30 ul reaction mixture. Filters are washed 3 times with 75 mM phosphoric acid followed by 2 washes with $H_2O$, and counted for 32P.

(1) The Km of CSBP for ATP was determined to be 170 uM. Therefore, compounds screened at the Km value of ATP.

(2) Compounds are usually dissolved in DMSO and are diluted in 25 mM Hepes buffer to get final concentration of DMSO of 0.17%.

Representative compounds of Formula (I), Examples I to 19, 30 and 31 have all demonstrated positive inhibitory activity of an $IC_{50}$ of <50 uM in this binding assay.

Prostoglandin Endoperoxide Synthase-2 (PGHS-2) Assay

The followiong assay describes a method for determining the inhibitory effects of compounds of Formula (I) on human PGHS-2 protein expression in LPS stimulated human monocytes. Method: Human peripheal blood monocytes were isolated from buffy coats by centrifugation through Ficoll and Percoll gradients. Cells were seeded at 2×10$^{6/}$well in 24 well plates and allowed to adhere for 1 hour in RPMI supplemented with 1% human AB serum, 20 mM L-glutamine, Penicillin-Streptomycin and 10 mM HEPES. Compounds were added at various concentrations and incubated at 37° C. for 10 minutes. LPS was added at 50 ng/well (to induce enzyme expression) and incubated overnight at 37° C. The supernatant was removed and cells washed once in cold PBS. The cells were lysed in 100 $\mu$l of cold lysis buffer(50 mM Tris/HCl pH 7.5, 150 mM NaCl, 1% NP40, 0.5% sodium deoxycholate, 0.1% SDS, 300 ug/ml DNAse, 0.1% TRITON X-100, 1 mM PMSF, 1 mM leupeptin, 1 mM pepstatin). The lysate was centrifuged (10,000 X g for 10 min. at 4° C.) to remove debris and the soluble fraction was subjected to SDS PAGE. analysis (12% gel). Protein separated on the gel were transferred onto nitrocellulose membrane by electrophoretic means for 2 hours at 60 volts. The membrane was pretreated for one hour in PBS/0.1% Tween 20 with 5% non-fat dry milk. After washing 3 times in PBS/Tween buffer, the membrane was incubated with a 1:2000 dilution of a monospecific antiserum to PGHS-2 or a 1:1000 dilution of an antiserum to PGHs-1 in PBS/Tween with 1% BSA for one hour with continuous shaking. The membrane was washed 3X in PBS/Tween and then incubated with a 1:3000 dilution of horseradish peroxidase conjugated donkey antiserum to rabbit 1 g (Amersham) in PBS/Tween with 1% BSA for one hour with continuous shaking. The membrane was then washed 3X in PBS/Tween and the ECL immunodetection system (Amersham) was used to detect the level of expression of prostaglandin endoperoxide synthases-2. Results: The following compounds were tested and found to be active in this assay (i.e., inhibited LPS induced PGHS-2 protein expression in rank order potency similar to that for inhibiting cytokine production as noted in assays indicated): 4-(4-Fluorophenyl)-2-(4-methylsulfinylphenyl)-5-(4-pyridyl)imidazole; 6-(4-Fluorophenyl)-2,3-dihydro-5-(4-pyridinyl)imidazo[2,1-b]thiazole; and Dexamethasone Several compounds were tested and found to be inactive (up to 10 uM): 2-(4-Methylsulfinylphenyl)-3-(4-pyridyl)-6,7-dihydro-(5H)-pyrrolo[1,2-a]imidazolerolipram; phenidone and NDGA. None of the compounds tested was found to inhibit PGHS-1 or $cPLA_2$ protein levels in similar experiments.

TNF-α in Traumatic Brain Injury Assay

The present assay provides for examination of the expression of tumor necrosis factor mRNA in specific brain regions which follow experimentally induced lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization is performed and quantitated relative to an TNF-α positive control RNA (macrophage=100%). A marked increase of TNF-α mRNA expression is observed in LH (104±17% of positive control, $p<0.05$ compared with sham), LC (105±21%, $p<0.05$) and LA (69±8%, $p<0.01$) in the traumatized hemisphere 1 hr. following injury. An increased TNF-α mRNA expression is also observed in LH (46±8%, $p<0.05$), LC (30±3%, $p<0.01$) and LA (32±3%, $p<0.01$) at 6 hr. which resolves by 24 hr. following injury. In the contralateral hemisphere, expression of TNF-α mRNA is increased in RH (46±2%, $p<0.01$), RC (4±3%) and RA (22±8%) at 1 hr. and in RH (28±11%), RC (7±5%) and RA (26±6%, $p<0.05$) at 6 hr. but not at 24 hr. following injury. In sham (surgery without injury) or naive animals, no consistent changes in expression of TNF-α mRNA is observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury Model for IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) were prepared. Total RNA is isolated and Northern blot hybridization is performed and the quantity of brain tissue IL-1β mRNA is presented as percent relative radioactivity of IL-1β positive macrophage RNA which is loaded on same gel. At 1 hr. following brain injury, a marked and significant increase in expression of IL-1β mRNA is observed in LC (20.0±0.7% of positive control, n=6, $p<0.05$ compared with sham animal), LH (24.5±0.9%, $p<0.05$) and LA (21.5±3.1%, $p<0.05$) in the injured hemisphere, which remained elevated up to 6 hr. post injury in the LC (4.0±0.4%, n=6, $p<0.05$) and LH (5.0±1.3%, $p<0.05$). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic pathologic or regenerative sequelae of brain injury.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (°C.). Mass spectra were performed upon a VG Zab mass spectrometer using fast atom bombardment or on a micromass platform electrospray ionization mass spectrometer in the positive ion mode using 95:5 $CH_3CNICH_3OH$ with 1% formic acid as the carrier solvent, unless otherwise indicated. $^1H$-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

Example 1

1-(4-Piperidinyl)-4-(4-fluorophenyl)-5-(2-2phenoxypyrimidin4-yl)imidazole a) 2-Methylthiopyrimidine-4-carboxaldehyde dimethyl acetal Pyruvic aldehyde dimethyl acetal (60 mL, 459 mmol) and N,N-dimethyl formamide dimethyl acetal (60 mnL, 459 mmol) were stirred together at 100° C. for 18 h. The mixture was cooled.

Methanol (300 mL), thiourea (69.6 g) and sodium methoxide (231 mL, 25 wt % in MeOH) were added to the above mixture and stirred at 70° C. for 2 h. After cooling, iodomethane (144 mL) was added dropwise and the mixture was stirred 3 h. at room temp. After diluting with EtOAc and $H_2O$, the organic phase was separated, dried ($Na_2SO_4$),and concentrated to yield the title compound as a brown oil (75.5 g, 82% yield). $^1H$ NMR ($CDCl_3$): d 8.17 (d, 1H), 6.77 (d, 1H), 5.15 (s, 1H), 3.40 (s, 6H).

b) 2-Methylthiopyrimidine-4-carboxaldehyde

The product of example 1(a) (9.96 g, 50 mmol), and 3 N HCl (42 mL, 126 mmol) were combined and stirred at 48° C. for 16 h, cooled to 23° C., combined with EtOAc (200 mL) and made basic by the addition of solid $Na_2CO_3$ (12.6 g, 150 mmol). The aqueous phase was extracted with EtOAc (4×150 mL, dried ($Na_2SO_4$), concentrated and the residue was filtered through a pad of silica (ca 150 mL) with $CH_2Cl_2$ to afford 7.49 g (97%) of the title compound $^1H$ NMR ($CDCl_3$): δ9.96 (s, 1), 8.77 (d, 1), 7.44 (d, 1), 2.62 (s, 3).

c) 1-t-Butoxycarbonyl-4-aminopiperidine 1-t-Butoxycarbonyl piperidine4-one (commercially available from Lancaster Chem) (39.9 g, 0.20 mol), THF (150 mL), $H_2O$ (300 mL), and $H_2NOH$ HCl (55.2, 0.80 mol) were dissolved together and $NA_2CO_3$ (55.2 g, 0.53 mol) was added in small portions. The mixture was stirred at 23° C. for 14 h, most of the THF was evaporated in vacuo, adjusted to pH>10 with 50% aq NaOH, extracted with EtOAc (5×50 mL) and concentrated to a white foam. Triturated with hexane, filtered and the solid was dried in vacuo to afford 40.31 g.

The above residue was dissolved in EtOH (abs) (1 L) and Raney Ni (50 mL of a slurry in EtOH) was added and the mixture was reduced under $H_2$ (50 psi) for 3.5 h. The catalyst was filtered off and washed with EtOH to afford. Concentration afforde 38.44 g (96% overall) of the title compound as a colorless oil which solidified to a white solid upon standing at −20° C.

d) 2-Methylthiopyrimidine-4-carboxaldehyde [1-t-butoxycarbonyl-4-aminopiperidine]imine The product of the previous step (6.51 g, 32.6 mmol) $MgSO_4$ (ca 2 g), the product of example 1(b) (4.84 g, 31.4 mmol), and $CH_2Cl_2$ (100 mL) were combined and stirred at 23° C. for 16 h. Filtration and concentration of the filtrate afforded the title compound as a yellow oil. $^1H$ NMR ($CDCl_3$): δ8.57 (d, 1), 8.27 (s, 1), 7.58 (d, 1), 4.05 (m, 2), 3.55 (m, 1), 3.00 (m, 2), 2.60 (s, 3), 1.75 (m, 4), 1.48 (s, 9).

e) 4-Fluorophenyl-tolylsulfonomethylformamide

To a suspension of p-toluenesulfinic acid sodium salt (30 g) in $H_2O$ (100 mL) was added methyl t-butyl ether (50 mL) followed by dropwise addition of conc HCl (15 mL). After stirring 5 min, the organic phase was removed and the aqueous phase was extracted with methyl t-butyl ether. The organic phase was dried ($Na_2SO_4$) and concentrated to near dryness. Hexane was added and the resulting precipitate collected to afford p-toluenesulfinic acid; yield 22 g. p-Toluenesulfinic acid (22 g, 140.6 mmol), p-fluorobenzaldehyde (22 mL, 206 mmol), formamide (20 mL, 503 mmol) and camphor sulphonic acid (4 g, 17.3 mmol) were combined and stirred at 60° C. 18 h. The resulting solid was broken up and stirred with a mixture of MeOH (35 mL) and hexane (82 mL) then filtered. The solid was resuspended in MeOH/hexanes (1:3, 200 mL) and stirred vigorously to break up the remaining chunks. Filtration afforded the title compound (27 g, 62% yield): $^1H$ NMR (400 MHz, $CDCl_3$) d 8.13 (s, 1H), 7.71 (d, 2H), 7.43 (dd, 2H), 7.32 (d, 2H), 7.08 (t, 2H), 6.34 (d, 1H), 2.45 (s, 3H).

f) 4-Fluorophenyl-tolylsulfonomethylisocyanide

4-Fluorophenyl-tolylsulfonomethylformamide (2.01 g, 6.25 mmol) in DME (32 mL) was cooled to −10° C. $POCl_3$ (1.52 mL, 16.3 mmol) was added followed by the dropwise addition of triethylamine (4.6 mL, 32.6 mmol) in DME (3 mL) keeping the internal temperature below −5° C. The mixture was gradually warmed to ambient temperature over 1 h, poured into $H_2O$ and extracted with EtOAc. The organic phase was washed with sat aq $NaHCO_3$, dried ($Na_2SO_4$), and concentrated. The resulting residue was triturated with petroleum ether and filtered to afford the title compound (1.7 g, 90% yield): $^1H$ NMR ($CDCl_3$) d 7.63 (d, 2H), 7.33 (m, 4H), 7.10 (t, 2H), 5.60 (s, 1H), 2.50 (s, 3H).

g) 1-[(1-t-Butoxycarbonyl)piperidin-4-yl]-4-(4-fluorophenyl)-5-[(2-methylthio(pyrimidin-4-yl)]imidazole The product of example 1(d) and the product of the previous example (9.41 g, 32.6 mmol), DMF (64 mL) and $K_2CO_3$ (4.43 g, 32.4 mmol) were combined and stirred for 2 days, diluted with $Et_2O$ and filtered. The solid was washed with $Et_2O$ and the filtrate was concentrated to a yellow solid. Trituration of the solid with $Et_2O$, filtration and washing with more $Et_2O$ and drying in vacuo afforded 9.07 g of the title compound as a white solid (62% from the product of example 1(b)). MS ES+m/z=470 ($MH^+$).

h) 1-[(1-t-Butoxycarbonyl)piperidin4-yl]-4-(4-fluorophenyl)-5-[(2-methylsulfonyl(pyrimidin-4-yl)] imidazole The product of the previous example (9.07 g, 19.3 mmol), dissolved in THF was cooled to −10° C. and OXONE (28.5 g, 46.4 mmol) in $H_2O$ (250 mL) was added dropwise. The resulting mixture was stirred at 23° C. for 24 h, combined with ice (100 mL) and $CH_2Cl_2$ (700 mL) shaken and the aqueous was separated. The organic phase was washed with brine (100 mL), dried ($Na_2SO_4$), concentrated and dried in vacuo to afford 8.27 g (85%) of the title compound as a white foam. MS ES+m/z=502 ($MH^+$).

i) 1-[(1-t-Butoxycarbonyl)piperidin-4-yl]4-(4-fluorophenyl)-5-(2-phenoxypyrimidin-4-yl)imidazole NaH (60% in mineral oil) (1.6 g, 40 mmol) was washed with dry THF and layered with more THF (75 mL) and phenol (4.14 g, 44 mmol) was added as a solid. The vigorous reaction subsided within 5 min and then the product of the previous example (5.01 g, 10 mmol) was added portionwise, and the reaction was stirred 90 min, concentrated in vacuo and the residue was dissolved in $CH_2Cl_2$ (300 mL) and washed with 10% aq NaOH (2x) and dried ($Na_2SO_4$), and filtered through a pad of silica gel with 0–2% MeOH in $CH_2Cl_2$, the desired fraction was concentrated and the residue was crystallized from acetone/hexane to afford 2.79 g (54%). MS ES+m/z=502 ($MH^+$).

j) 1-(4-Piperidinyl)-4-(4-fluorophenyl)-5-(2-phenoxypyrimidin-4-yl)imidazole

The product of the previous example (3.91 g, 7.59 mmol) was combined with ice cold TFA (75 mL) and then warmed to 23° C. and stirred for 15 min, and the reaction was concentrated in vacuo and the residue was dissolved in EtOAc (200 mL) and washed with 10% aq NaOH (2×100 mL), dried ($Na_2SO_4$) concentrated and the residue was crystallized from acetone/hexane to afford 2.24 g (71%) the title compound as white crystals. mp=182–183° C.

Example 2

1-(4-Piperidinyl)-4-(4-fluorophenyl)-5-(2-phenoxy4-pyridinyl)imidazole a) 2-Chloro-4-hydroxymethylpyridine To a suspension of $NaBH_4$ (4.66 g 123 mmol) in THF (400 mL) at 0° C. was added 2-chloro-4-pyridinedcarboxylic acid (12.9 g, 82.1 mmol) portionwise. The resulting solution was allowed to warm to room temperature and stirred for 1.5 h after which was added a solution of $BF_3O(Et)_2$ (19.2 mL, 156 mmol) in THF (125 mL) over 3 h. The reaction was stirrred at room temperature for an additional 20 h, cooled to 0° C. and 1.5 N HCl (100 mL) was added dropwise. The reaction was allowed to warm to room temperature, the THF was evaporated under reduced pressure and 4 N NaOH solution was added to adjust the pH to 10 to 11. The solution was extracted with EtOAc thrice and the organic layers were washed with a saturated solution of NaCl. The organic layers were combined, dried over magnesium sulfate, filtered, and concentrated under reduced pressure to give the title compound as a white solid (10.8 g, 92% yield). $^1H$ NMR ($CDCl_3$): δ8.30 (d, 1H, J=4.9 Hz), 7.37 (s, 1H), 7.22 (d, 1H, J=4.9 Hz), 4.76 (s, 2H), 2.50 (br-s, 1H).

b) 2-Chloro4-pyridinecarboxaldehyde

A suspension of 2-chloro-4-hydroxymethylpyridine (8.0 g, 55.9 mmol), NBS (14.9 g, 83.9 mmol), and $K_2CO_3$ (11.75 g, 97.1 mmol) in ethyl acetate was refluxed for 3 h. Another portion of NBS (14.9 g, 83.9 mmol) and $Na_2CO_3$ (12.0 g, 114 mmol) was added and heating was continued another 3.5 h. The reaction mixture was cooled, filtered through a pad of celite, concentrated under reduced and chromatographed with 0.5–4% $CH_3OH/CH_2Cl_2$. The combined fractions were washed with $NaHCO_3$ (sat.), 10% $Na_2S_2O_3$, and NaCl (sat.), dried, filtered and evaporated to give the title compound as a light yellow solid (5.3 g, 67% yield). $^1H$ NMR ($CDCl_3$): δ10.06 (s, 1H), 8.66 (d, 1H, J=5.0 Hz), 7.76 (s, 1H), 7.66 (d, 1H, J=5.0 Hz).

c) 2-Chloro-4-pyridinecarboxaldehyde(1-t-butoxycarbonyl-4-aminopiperdine)imine

Following the procedure of example 1(d) except using 2-chloro-4-pyridinecarboxaldehyde afforded the title compound. $^1$H NMR ($CDCl_3$): δ8.45 (d, 1H, J=5.1 Hz), 8.29 (s, 1H), 7.65 (s, 1H), 7.52 (d, 1H, J=5.1 Hz), 4.05 (br-s, 2H), 3.48 (m, 1H), 3.03(m, 2H), 1.73 (m, 4H), 1.48 (s, 9H).

d) 1-(1-t-Butoxycarbonyl-4-piperidinyl)-4-(4-fluorophenyl)-5-(2-chloro-4-pyridinyl)imidazole Following the procedure of example 1(g) except using the compound from the previous step afforded the title compound which was purified by flash chromatography with 0–5% $CH_3OH/CH_2Cl_2$ and then recrystallized from ethyl ecetate/hexanes to give a light yellow solid.

e) 1-(1-t-Butoxycarbonyl-4-piperidinyl)-4-(4-fluorophenyl)-5-(2-phenoxy-4-pyridinyl)imidazole To a stirring suspension of NaH (120 mg, 3.0 mmol) in DMA (1.3 mL) was added phenol (0.40 g, 4.25 mmol). After the bubbling cease, 1-(1-t-butoxycarbonyl-4-piperidinyl)-4 (4-fluorophenyl)-5-(2-chloro-4-pyridinyl)imidazole (0.20 g, 0.44 mmol) was added and the resulting solution was heated at 120° C. until no evidence of starting material was seen by mass spectroscopy (1–3 days). To the cooled solution was added 1 M NaOH and the mixture was extracted thrice with EtOAc. The combined organic layers were washed with NaCl (sat.), dried over $MgSO_4$, filtered, and evaporated under reduced pressure to give a light yellow solid. The solid was then chromatographed with 50–80% EtOAc/Hex to give the title compound as a white solid (143 mg, 64% yield). ES (+) MS m/e=515 ($MH^+$)

f) 1-(4-Piperidiny)-4-(4-fluorophenyl)-5-(2-phenoxy-4-pyridinyl)imidazole

To the compound from the previous step (143 mg, 0.28 mmol) was added a cooled solution of TFA (10 mL) at −10° C. The reaction was allowed to warm to room temperature, stirred 30 min at room temperature, and evaporated under reduced pressure to give an orange oil which was dissolved in water (10 mL) and add 3 N HCl (0.5 mL). The water layer was washed twice with EtOAc, made basic with 50% NaOH, and extracted the aqueous layer thrice with EtOAc. The combined organic layers were washed with NaCl, dried over $MgSO_4$, filtered and evaporated under reduced pressure to give a white foam (80 mg, 70%). ES (+) MS m/e=415 ($MH^+$).

Example 3

1-(4-piperidinyl)-4-(4-fluorophenyl)-5-[2-(4-methoxyphenoxy)-4-pyridinyl]imidazole Following the procedure of examples 2e and 2f except using 4-methoxyphenol afforded the title compound as a white foam in 74% yield for the two steps. ES (+) MS m/e=445 ($MH^+$).

Example 4

1-(4-piperidinyl)-4-(4-fluorophenyl)-5-[2-(4-fluorophenoxy-4-pyridinyl]imidazole Following the procedure of examples 2e and 2f except using 4-fluorophenol afforded the title compound as a white foam in 35% yield for the two steps. ES (+) MS m/e=433 ($MH^+$).

Example 5

1-(Piperidin-4-yl)-4-(4-fluophenyl)-5-[2-(4-methoxyphenoxy)pyrimidin-4-yl]imidazole The title compound was prepared by the method of examples 1(i) and 1(j) except using 4-methoxyphenol. mp=190–191°.

Example 6

1-(Piperidin-4-yl)-4-(4-fluorophenyl)-5-[2-(4-fluorophenoxy)pyrimidin-4-yl]-imidazole The title compound was prepared by the method of examples 1(i) and 1(j) except using 4-fluorophenol. mp=186–187°.

Example 7

1-(Pieridin-4-yl)-4-(4-fluorophenyl)-5-[2-(4-aminocarbonylphenoxy)pyrimidin-4-yl]imidazole The title compound was prepared by the method of examples 1(i) and 1(j) except using 4-hydroxybenzamide. mp=229–230°.

Example 8

1-(Piperidin-4-yl)-4-(4-fluorophenyl)-5-[2-(4-ethylphenoxy)pyrimidin-4-yl]imidazole The title compound was prepared by the method of examples 1(i) and 1(j) except using 4-ethylphenol. mp=173–174.

Example 9

1-(Piperidin-4-yl )-4-(4-fluorolphenyl)-5-[2-(4-benzyloxylphenoxy)pyrimidin-4-yl]imidazole The title compound was prepared by the method of examples 1(i) and 1(j) except using 4-benzyloxyphenol. mp=178–179°.

Example 10

1-(Piperidin-4-yl)-4-(4-fluorophenyl)-5-[2-(4-cyanophenoxy)pyrimidin-4-yl]imidazole The title compound was prepared by the method of examples 1(i) and 1(j) except using 4-cyanophenol. mp=192–193°.

Example 11

1-(Piperidin-4-yl)-4-(4-fluorophenyl)-5-[2-(4-hydroxyphenoxy)pyrimidin-4-yl]imidazole The title compound was prepared by the method of examples 1(i) and 1(j) except using hydroquinone. mp=255–260° (dec).

Example 12

1-(4-Hydroxycyclohexyl)-4-(4-fluorophenyl)-5-[2-(4-phenoxy)pyrimidin-4-yl]imidazole a) 1-Amino-4-(1,3-dioxycyclopentyl)cyclohexane To a mixture of 1,4-cyclohexanedione monoethylene ketal (27.6 g, 177 mmol) and hydroxylamine hydrochloride (49.2 g, 708 mmol) in $H_2O$ (250 mL) was added portionwise $Na_2CO_3$ (49.2 g, 547 mmol). After stirring 1 h, the mixture was extracted with EtOAc. The organic phase was dried ($Na_2SO_4$) and concentrated affording 4-(1,3-dioxycyclopentyl)-cyclohexanone oxime (27.5 g, 90% yield).

The oxime (27.5 g, 161 mmol), Raney Ni (ca 13.5 mL as a suspension in EtOH) and EtOH (200 mL) were combined and shaken at 50 psi $H_2$ for 4 h. The catalyst was filtered off and the filtrate was concentrated to afford the title compound as a colorless oil (23.6 g, 93% yield). $^1$H NMR ($CDCl_3$): δ2.64 (m, 1H), 1.75–1.25 (m, 12 H).

b) 2-Methylthiopyrimidine-4-carboxaldehyde(4-ethylene ketal cyclohexyl)imine

A mixture of 2-methylthiopyrimidine-4-carboxaldehyde (9.5 g, 6.9 mmol) prepared in example 1(b) and 1-amino4-(1,3-dioxycyclopentyl)cyclohexane (10.8 g, 6.9 mmol) from the previous step were stirred in DMF (150 mL) 18 h. The title compound was used without any purification. $^1$H NMR ($CDCl_3$): δ8.51 (d, 1H), 8,21 (s, 1H), 7.53 (d, 1H), 3.93, (s, 4H), 3.40 (m, 1H), 2.55 (s, 3H), 1.94–1.70 (m, 6H), 1.61 (m, 2H).

c) 1-(4-Ethylene ketal cyclohexyl)imidazole-4-(4-fluorophenyl)-5-[(2-methylthio)pyrimidin-4-yl]imidazole To the crude product from the previous example in DMF cooled to 0° C. was added 4-fluorophenyl-tolylsulfonomethylisocyanide prepared in example 1(f) (26 g, 90 mmol) and $K_2CO_3$ (15.7 g, 113.6 mmol). The mixture was stirred at 0° C. for 3 h. then gradually warmed to room temp. and stirred for 18 h. EtOAc was added and the mixture was filtered washing the solid with EtOAc. $H_2O$ was added to the filtrate and the organic phase was separated, dried ($Na_2SO_4$). and concentrated. The mixture was evaporated to near dryness and filtered washing with 1:1 EtOAc/ to afford the title compound as pale yellow crystals. $^1$H NMR ($CDCl_3$): δ8.33 (d, 1H), 7.81 (s, 1H), 7.43 (q, 2H), 7.12 (t, 2H), 6.78 (d, 1H), 4.74 (m, 1H), 4.00 (s, 4H), 2.59 (s, 3H), 2.18 (dd, 2H), 2.04 (dq, 2H), 1.89 (dd, 2H), 1.70 (dt, 2H).

d) 1-(4-Ethylene ketal cyclohexyl)]-4-(4-fluorophenyl)-5-[(2-methylsulfoxy)pyrimidin-4-yl]imidazole To a solution of the compound from the previous step (0.20 g, 0.48 mmol) in THF (2 mL) and MeOH (1 mL) at 0° C. was added OXONE (0.36 g, 0.56 mmol) dissolved in $H_2O$ (2 mL). The mixture was stirred for 0.5 h. then poured into 10% NaOH and extracted with EtOAc. The organic phase was dried ($Na_2SO_4$) and concentrated. The resulting residue was triturated with $Et_2O$ and filtered affording the title compound as a white solid (0.089 g, 45% yield) $^1$H NMR ($CDCl_3$): δ8.36 (d, 1H), 7.82 (s, 1H), 7.42 (q, 2H), 7.02 (t, 2H), 6.79 (d, 1H), 4.80 (m, 1H), 4.00 (s, 3H), 2.20 (m, 2H), 2.06 (m, 3H), 1.89 (m, 2H), 1.70 (m, 5H).

e) 1-(4-Ethylene ketal cyclohexyl)-4-(4-fluorophenyl)-5-[(2-phenoxy)pyrimidin4-yl]imidazole Phenol (0.43 g., 4.6 mmol) was added to a suspension of sodium hydride (0.18 g., 60%, 4.6 mmol) in dry THF (6 mL). When gas evolution ceased the sulfoxide of the previous step (0.242 g., 2.3 mmol) was added and the mixture was stirred overnight. The mixture was quenched with water and extracted with ethylacetate. EtOAc. The organic phase was dried ($Na_2SO_4$) and concentrated. The residue was triturated with EtOAc/hexane to give the title compound as a white solid (0.628 g, 57% yield). 1H NMR ($CDCl_3$): d 8.40 (d, 1H), 7.97 (s, 1H), 7.45 (m, 4H), 7.27 (m,3H), 7.04 (t, 2H), 6.85 (d, 1H), 4.57 (m, 1H), 3.99 (t, 4H), 1.89 (m, 4H), 1.72 (d, 2H), 1.43 (m, 2H).

f) 1-(4-Oxocyclohexyl)4-(4-fluorophenyl)-5-[(2-phenoxy)pyrimidin-4-yl]imidazole

A mixture of the compound from the previous step (0.628 g, 1.3 mmol) in 3N HCl (6 mL) was stirred 36 h. then neutralized with saturated aqueous $Na_2CO_3$ and filtered. The solid was washed with water and the aqueous mixture was extracted with EtOAc. The organic phase was dried ($Na_2SO_4$) and concentrated giving the title compound as white crystals (0.439 g. 79 %). IR (neat) 1717, 1570, 1506. 1H NMR ($CDCl_3$) 8.41 (d, 1HO, 7.72 (s, 1H), 7.46 (m, 4H), 7.29 (m, 3H), 7.08(t, 2H), 6.90 (d, 1H), 5.09 (m, 1H), 2.37 (dd, 2H), 2.24 (m, 2H0, 2.15 (dt, 2H), 2.02 (dq, 2H)

g) trans-1-(4-Hydroxycyclohexyl)-4-(4-fluorophenyl)-5-[(2-phenoxy)pyrimidin-4-yl]imidazole To a solution of the compound in above example (0.439 g, 1.03 mmol) in MeOH/THF (1 mL, 1:1) was added $NaBH_4$ solution [1mL, 1M sln. made by combining 1.52 g, $NaBH_4$, MeOH (30 mL), and 25% NaOMe in MeOH (2 mL)]. After stirring 30 min., the mixture was quenched with saturated $Na_2CO_3$ and the solvent was evaporated. The residue was recrystalized from MeOH/$H_2O$ to afford the title compound as white needles (0.275 g, 64% yield). mp 212–215° C. 1H NMR ($CDCl_3$) 8.40 (d, 1H), 7.70(s, 1H), 7.44(m, 4H), 7.28(m, 3H), 7.05(t, 2H), 6.85(d, 1H), 4.51(m, 1H), 3.63(m, 1H), 1.96(d, 4H), 1.62 (q, 2H), 1.17(q, 2H)

Example 13

1-(Piperidin-4-yl)-4-(4-fluorolphenyl)-5-[2-(2,6-dimethylphenoxy)pyridin-4-yl]imidazole Following the procedure of examples 2(e) and 2(f) except using 2,6-dimethylphenol afforded the title compound as a white foam in 34% yield for the two steps. ES (+) MS m/e=443 ($MH^+$).

Example 14

1-(Piperidin-4-yl)4-(4-fluorophenyl)-5-[2-(4-methylphenoxy)pyridin-4-yl]imidazole Following the procedure of examples2(e) and 2(f) except using 4-methylphenol afforded the title compound as a white foam in 49% yield for the two steps. ES (+) MS m/e=429 ($MH^+$).

Example 15

1-(Piperidin-4-yl)4-(4-fluorophenyl)-5-[2-(4-chlorophenoxy)pyridin-4-yl]imidazole Following the procedure of examples 2(e) and 2(f) except using 4-chlorophenol afforded the title compound as a white foam in 46% yield for the two steps. ES (+) MS m/e=449 ($MH^+$).

Example 16

1-[3-(N-Morpholino)propyl]-4-(4-fluorophenyl)-5-[2-(phenoxy)pyrimidin-4-yl]imidazole a) 2-Methylthiopyrinidine-4-carboxaldehyde 3-(N-morpholino)propylamine imine The product of example 1(d) (2.75g, 17.8 mmol) and N-(aminopropyl)morpholine (2.87 mL, 19.4 mmol) $CH_2Cl_2$ (75 mL), and some $MgSO_4$ were mixed and stirred for 16 h, filtered and concentrated to afford a brown oil. 1H NMR ($CDCl_3$): d 8.57 (d, 1), 8.23 (s, 1), 7.55 (d, 1), 3.73 (m, 6), 2.58 (s, 3), 2.42 (m, 6), 1.91 (m, 2).

b) 1-[3-(N-Morpholino)propyl]-4-(4-fluorophenyl)-5-[2-(methylthio)-pyrimidin4-yl]imidazole The product of the preceding example and the product of example 1(f) were reacted by the procedure of example 1(g) to afford 5.3 g (72% from the product of example 1(d)). 1H NMR (CDCl3): d 8.32 (d, 1), 7.67 (s, 1), 7.46 (m, 2), 7.04 (t, 2), 6.80 (d, 1), 4.42 (t,2), 3.69 (m, 4), 2.60 (s, 3), 2.38 (m, 4), 2.29 (t, 2), 1.86 (m, 2).

c) 1-[3-(N-Morpholino)propyl]-4-(4-fluorophenyl)-5-[2-(phenoxy)pyrimidin-4-yl]imidazole The product of the preceeding example was reacted by the procedure of example 1(h) and 1(i) to afford the title compound as a waxy solid. mp=95–96.

Examlple 17

1-(Piperidin-4-yl)-4-(4-fluorophenyl)-5-[2-(3-methoxyphenoxy)pyrimidin-4-yl]imidazole The title compound was prepared by the method of examples 1(i) and 1(j) except using 3-methoxyphenol. mp=117–118°.

Example 18

1-(Piperidin-4-yl)-4-(4-fluorophenyl)-5-[2-(4-phenylphenoxy)pyrimidin-4-yl]imidazole The title compound was prepared by the method of examples 1(i) and 1(j) except using 4-phenylphenol. mp=192–193°.

Example 19

1-(Piperidin-4-yl)-4-(4-fluorolphenyl)-5-[2-(4-phenoxyphenoxy)pyrimidin-4-yl]imidazole The title compound was prepared by the method of examples 1(i) and 1(j) except using 4-phenyloxyphenol. mp=174–175°.

Example 20

1-(Piperidin-4-yl)-4-(4-fluorolphenyl)-5-[2-(3-hydroxyphenoxy)pyrimidin-4-yl]imidazole The title compound was prepared by the method of examples 1(i) and 1(j) except using resorcinol. MS ES+m/z=431 ($MH^+$).

Example 21

1-(3-N-Morpholinyl-1-propyl)-4-(4-fluorophenyl)-5-[2-(4-fluorophenoxy)pyrimidin-4-yl]imidazole The title compound was prepared by the method of example 16 except using 4-fluorophenol. MS ES+m/z=278 (MH+).

Example 22

1-(Piperidin-4-yl)4-(4-fluorophenyl)-5-[2-(2-hydroxyphenoxy)pyrimidin-4-yl]imidazole The title compound was prepared by the method of examples 1(i) and 1(j) except using catechol. MS ES+m/z=431 (MH+).

Example 23

1-(Piperidin-4-yl)-4-(4-fluorophenyl)-5-[2-((3,4-methylenedioxy)phenoxy)pyrimidin-4-yl]imidazole The title compound was prepared by the method of examples 1(i) and 1(j) except using sesamol. mp=131–132°.

Example 24

1-(Piperidin-4-yl)4-(4-fluorophenyl)-5-[2-(3-fluorophenoxy)pyrimidin-4-yl]imidazole The title compound was prepared by the method of examples 1(i) and 1(j) except using 3-fluorophenol. mp=155–156°.

Example 25

1-(Piperidin-4-yl)-4-(4-fluorophenyl)-5-[2-(2-fluorophenoxy)pyrimidin-4-yl]imidazole The title compound was prepared by the method of examples 1(i) and 1(j) except using 2-fluorophenol. mp=154–155°.

Example 26

1-(Piperidin-4yl)-4-(4-fluorophenyl)-5-[2-(2-methoxyphenoxy)pyrimidin-4-yl]imidazole The title compound was prepared by the method of examples 1(i) and 1(j) except using 2-methoxyphenol. MS ES+m/z=446 (MH+).

Example 27

1-(Piperidin-4-yl)-4-(4-fluorophenyl)-5-[2-(3-trifluoromethylphenoxy)pyrimidin-4-yl]imidazole The title compound was prepared by the method of examples 1(i) and 1(j) except using 3-trifluoromethylphenol. mp=137–138°.

Example 28

1-(Piperidin-4-yl)-4-(4-fluorophenyl)-5-[2-(3,4-difluorophenoxy)pyrimidin-4-yl]imidazole The title compound was prepared by the method of examples 1(i) and 1(j) except using 3,4-difluorophenol. MS ES+m/z=452 (MH+).

Example 29

1-(Piperidin-4-yl)-4-(4-fluorolphenyl)-5-[2-(4-methylsulfonylphenoxy)pyrimidin-4-yl]imidazole The title compound was prepared by the method of examples 1(i) and 1(j) except using 4-methylsulfonylphenol. MS ES+m/z=494 (MH+).

Example 30

1-(Piperidin-4-yl)-4-(4-fluorophenyl)-5-[(2-(phenylthio)pyridin-4-yl]imidazole

Following the procedure of examples 2(e) and 2(f) except using thiophenol afforded the title compound as a yellow foam in 36% yield for the two steps. ES (+) MS m/e=431 ($MH^+$)

Example 31

1-(Piperidin-4-yl)-4-(4-fluorophenyl)-5-[(2-(1-methyltetrazol-5-ylthio)pyridin4-yl]imidazole;

Following the procedure of examples 2(e) and 2(f) except using 5-mercapto-1-methyltetrazole afforded the title compound as a light yellow foam. The foam was further purified by reverse phase cromatography with 60–70% $CH_3CN/H_2O$ and 0.1% TFA. The relevant fractions were combined and made basic with 1M NaOH and extracted thrice with EtOAc. The combined organic layers were dried over $MgSO_4$, filtered, and evaporated under reduced pressure to give an off-white foam in 13% yield for the two steps. ES (+) MS m/e=437 ($MH^+$)

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows:

What is claimed is:

1. A compound represented by the formula:

(I)

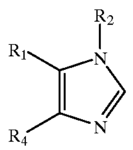

$R_1$ is a quinolyl, or isoquinolinyl ring, which ring is substituted with Y—$R_a$ and optionally with an additional independent substituent selected from $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_b$ or $NHR_a$;

Y is oxygen or sulfur;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substitiuent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_2$ is —$(CR_{10}R_{20})_{n'}$ $OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl-$C_{1-10}$-alkyl, aryl, aryl$C_{1-10}$ alkyl, heteroamyl, heteroaryl-$C_{1-10}$-alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR^{13}R_{14}$, $(CR_{10}R_{20})_nC(Z)R_{11}$, $(CR_{10}R_{20})_nOC(Z)R_{11}$, $(CR_{10}R_{20}O)_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-$(R_{18})$-1,2,4-oxadizaol-3-yl or 4-$(R_{12})$-5-$(R_{18}R_{19}$-4,5-dihydro-1,2,4-oxadiazol-3-yl; wherein ihe aryl, arylalkyl, cycloalkyl, cycloalkylakyl, heteroaryl, heteroaryl allyl, heterocyclic and heterocyclic alkyl groups may be optionally substituted;

n is an integer having a value of 1 to 10;

n' is 0, or an integer having a value of 1 to 10;

Z is oxygen or sulfur;

$R_a$ is aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$, heterocyclyl, or heterocyclyl$C_{1-4}$ alkyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$SOR_5$ being —SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$cycloalkyl, $C_{5-7}$ cycloalkenyl, aryl, aryl$C_{1-10}$ alkyl, heteroaryl, heteroaryl$C_{1-10}$alkyl, $(CR_{10}R_{20})_nOR_{11}$ $(CR_{10}R_{20})_nS(O)_mR_{18}$, $(CR_{10},R_{20})_nNHS(O)_2R_{18}$, $(CR_{10}R_{20})_nNR_{13}R_{14}$; wherein the aryl, arylalkyl, heteroaryl, and heteroaryl alkyl groups may be optionally substituted;

$R_9$ is hydrogen, —$C(Z)R_{11}$ or optionally substituted $C_{1-10}$ alkyl, $S(O)_2R_{18}$, optionally substituted aryl or optionally substituted aryl-$C_{1-4}$ alkyl;

$R^{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or C(Z)—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl;

$R_{19}$ is hydrogen, cyano, $C_{1-4}$ alkyl, $C_{3-7}$ cycloalkyl or aryl; or a pharmaceutically acceptable salt thereof.

2. The compound according to claim 1 wherein Y is oxygen.

3. The compound according to claim 2 wherein the $R_a$ moiety is optionally substituted one or more times with halogen; $C_{1-4}$ alkyl; halosubstituted alkyl; hydroxy; hydroxy substituted $C_{1-4}$ alkyl; $C_{1-4}$ alkoxy; $S(O)_m$alkyl and $S(O)_m$aryl (wherein m is 0, 1, or 2); $C(O)OR_{11}$; $C(O)R_{11}$; —$OC(O)R_c$; —O—$(CH_2)$s—O; amino; mono-and di-$C_{1-6}$ alkylsubstituted amino; —$N(R_{10})C(O)R_b$; —$C(O)NR_{10}R_{10}R_{20}$; cyano, nitro, N-heterocyclyl ring which ring has from 5 to 7 members and optionally contains an additional heteroatom selected from oxygen, sulfur or $NR_{15}$; aryl; arylalkyl; aryloxy; or arylalkyloxy; and s is 1 to 3: wherein $R_c$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or a heterocyclyl$C_{1-4}$ alkyl moiety, all of which moieties may be optionally substituted.

4. The compound according to claim 3 wherein the substituent is halogen, halosusbsituted alkyl, hydroxy, cyano, alkyl, aryl, alkoxy, aryloxy, arylalkyloxy, alkylthio, alkylsulfonyl, aminocarbonyl, methylenedioxy, tetrazole, or methyltetrazolyl.

5. The compound according to claim 2 wherein $R_4$ is an optionally substituted phenyl.

6. The compound according to claim 5 wherein the phenyl is substituted one or more times independently by halogen, —$SR_5$, —$S(O)R_5$, —$OR_{12}$, halo-substituted-$C_{1-4}$-alkyl, or $C_{1-4}$ alkyl.

7. The compound according to claim 1 wherein $R_2$ is selected from optionally substituted $C_{1-10}$ alkyl, optionally substituted heterocylcyl, optionally substiuted heterocyclyl$C_{1-10}$ alkyl, optionally substituted $C_{3-7}$cycloalkyl, or optionally substituted $C_{3-7}$cycloalkyl $C_{1-10}$ alkyl.

8. The compound according to claim 7 wherein $R_2$ is an optionally substituted heterocylcyl, or optionally substiuted heterocyclyl$C_{1-10}$ alkyl.

9. The compound according to claim 8 wherein substitutents are independently selected from halogen; $C_{1-4}$ alkyl; aryl; arylalkyl; $C(O)OR_{11}$; C(O)H; $C(O)C_{1-4}$ alkyl; hydroxy substituted $C_{1-10}$ alkyl; $C_{1-10}$ alkoxy; $S(O)_mC_{1-4}$ alkyl (wherein m is 0, 1, or 2), or $NR_{10}R_{20}$.

10. The compound according to claim 8 wherein $R_2$ is morpholino propyl, piperidine, N-methylpiperidine, N-benzylpiperidine, 2,2,6,6-tetramethylpiperidine, 4-aminopiperidine, or 4-amino-2,2,6,6-tetramethyl piperidine.

11. The compound according to claim 7 wherein $R_2$ is an optionally substituted $C_{3-7}$cycloalkyl, or optionally substituted $C_{3-7}$cycloalkyl $C_{1-10}$ alkyl.

12. The compound according to claim 11 wherein the optional substituents are independently selected from halogen; hydroxy; $C_{1-10}$ alkoxy; $S(O)_m$ alkyl, wherein m is 0, 1, or 2; $S(O)_m$ aryl; cyano; nitro; $NR_7R_{17}$ group; $N(R_{10})C(O)X_1$ and $X_l$ is $C_{1-4}$ alkyl, aryl or aryl$C_{1-4}$alkyl; $C_{1-10}$ alkyl; optionally substituted alkyl wherein the substituents are halogen, hydroxy, nitro, cyano, $NR_7R_{17}$ group, S(O)m alkyl and S(O)m aryl; optionally substituted alkylene; optinally substituted alkyne; $C(O)OR_{11}$; the group $R_e$; —C(O)H; =O; =N—$OR_{11}$; —NH)—OH (or substituted alkyl or aryl derivatives thereof on the nitrogen or the oxime moiety); —$N(OR_d)$—C(O)—$R_f$, optionally substituted aryl; an optionally substituted aryl$C_{1-4}$alkyl; optionally substituted heterocycle or heterocyclic $C_{1-4}$alkyl;

wherein $R_d$ is hydrogen, a pharmaceutically acceptable cation, aroyl or a $C_{1-10}$ alkanoyl;

$R_e$ is a 1,3-dioxyalkylene group of the formula —O—$(CH_2)_s$—O—, wherein s is 1 to 3;

$R_f$ is $NR_{21}R_{22}$; alkyl 1–6; halosubstituted alkyl 1–6; hydroxy substituted alkyl 1–6; alkenyl$_{2-6}$; aryl or heteroaryl optionally substituted by halogen, alkyl 1–6, halosubstituted alkyl$_{1-6}$, hydroxyl, or alkoxy $_{1-6}$;

$R_{21}$ is hydrogen, or alkyl$_{1-6}$;

$R_{22}$ is hydrogen, alkyl$_{1-6}$, aryl, benyl, heteroaryl, alkyl substituted by halogen or hydroxyl, or phenyl substituted by a member selected from the group consisting of halo, cyano, alkyl-$_{1-12}$, alkoxy $_{1-6}$, halosubstituted alkyl$_{1-6}$, alkyithio, alkylsulphonyl, or alkylsulfinyl; or $R_{21}$ and $R_{22}$ may together with the nitrogen to which they are attached form a ring having 5 to 7 members, which members may be optionally replaced by a heteroatom selected fom oxygen, sulfur or nitrogen.

13. The compound according to claim 11 wherein $R_2$ is hydroxycyclohexyl, 4-methyl-4-hydroxycyclohexyl, 4-pyrrolinindyl-cyclohexyl, 4-methyl-4-aminocyclohexyl, 4-methyl-4-acetamidocyclohexyl, 4-keto cyclohexyl, 4-oxiranyl, or 4-hydroxy-4(1-propynyl)cyclohexyl.

14. A pharmaceutical composition comprising a compound according to claim 1 and a pharmaceutically acceptable carrier or diluent.

15. A method of treating a CSBP/PK/p38 kinase mediated disease in a mammal in need thereof, which method comprises administering to said mammal an effective amount of a compound of Formula (I) according to claim 1.

16. The method according to claim 15 wherein the CSBP/RK/p38 kinase mediated disease is psoriatic arthritis, Reiter's syndrome, rheumatoid arthritis, gout, traumatic arthritis, rubella arthritis and acute synovitis, rheumatoid arthritis, rheumatoid spondylitis, osteoarthritis, gouty arthritis and other arthritic condition, sepsis, septic shock, endotoxic shock, gram negative sepsis, toxic shock syndrome, stroke, neurotrauma, asthma, adult respiratory distress syndrome, cerebral malaria, chronic pulmonary inflammatory disease, silicosis, pulmonary sarcososis, bone resorption disease, osteoporosis, restenosis, cardiac and renal reperfusion injury, thrombosis, glomerularnephritis, diabetes, graft vs. host reaction, allograft rejection, inflammatory bowel disease, Crohn's disease, ulcerative colitis, muscle degeneration, eczema, contact dermititis, psoriasis, sunburn, or conjunctivitis.

17. A method of treating inflammation in a mammal in need thereof, which method comprises administering to said mammal an effective amount of a compound of Formula (I) according to claim 1.

18. A method of treating osteoporosis in a mammal in need thereof, which method comprises administering to said mammal an effective amount or a compound of Formula (I) according to claim 1.

19. A process for preparing a compound of Formula (I) as defined in claim 1 which comprises reacting a compound of the Formula (II):

(II)

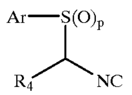

with a compound of the Formula (III):

(III)

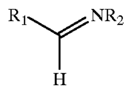

wherein p is 0 or 2; and a base strong enough to deprotonate the isonitrile moiety of Formula (II); and $R_1$, $R_2$ and $R_4$ are as defined in claim 1 or are precursors of the groups $R_1$, $R_2$ and $R_4$ and Ar is an optionally substituted phenyl group, and thereafter if necessary, converting a precursor of $R_1$, $R_2$ and R4 to a group $R_1$, $R_2$ and $R_4$.

20. The process according to claim 19 when p=0.

21. The process according to claim 19 when p=2.

22. The process according to claim 19 wherein the imine of Formula (III), is isolated prior to reaction with Formula (II).

23. The process according to claim 22 wherein the imine of Formula (III), is formed in situ prior to reaction with Formula (II).

24. The process according to claim 23 wherein the imine is formed in situ by reacting an aldehyde of the formula $R_1CHO$, wherein $R_1$ is as defined for Formula (I), with a primary amine of the formula $R_2NH_2$, wherein $R_2$ is as defined for Formula (I).

25. The process according to claim 24 wherein formation of the imine in situ utilizes dehydrating conditions.

26. The process according to claim 24 wherein the solvent is N,N-dimethyl-formamide (DMF), halogenated solvents, tetrahydrofuran (THF), dimethylsulfoxide (DMSO), alcohols, benzene, toluene, MeCN, or DME.

27. The process according to claim 24 wherein $R_2$ in the primary amine $R_2NH_2$ is piperidine, 1-Formyl-4-piperidine, 1-benzyl-4-piperidine, 1-methyl-4-piperidine, 1-ethoxycarbonyl-4-piperidine, 1-t-butoxvcarbonyl-4-piperidine, 2,2,6,6-tetramethyl4-piperidine, morpholino ethyl, morpholino propyl, pyrrolidinyl propyl, or piperidinyl propyl.

28. The compound according to claim 1 wherein $R_a$ is an optionally substituted aryl or arylalkyl.

29. The compound according to claim 2 wherein $R_a$ is an optionally substituted aryl or arylalkyl.

30. The process according to claim 21 wherein the base is an amine, a carbonate, a hydride, or an alkyl or aryl lithium reagent.

* * * * *